US008795266B2

(12) United States Patent  
Esch et al.

(10) Patent No.: US 8,795,266 B2  
(45) Date of Patent: *Aug. 5, 2014

(54) METHODS AND APPARATUS FOR COAGULATING AND/OR CONSTRICTING HOLLOW ANATOMICAL STRUCTURES

(71) Applicant: Covidien LP, Mansfield, MA (US)

(72) Inventors: Brady D. Esch, San Jose, CA (US); Bob McRae, San Jose, CA (US); Arthur W. Zikorus, San Jose, CA (US); Michael S. Mirizzi, San Jose, CA (US); Christopher Scott Jones, Menlo Park, CA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/723,464

(22) Filed: Dec. 21, 2012

(65) Prior Publication Data

US 2014/0012245 A1 Jan. 9, 2014

Related U.S. Application Data

(63) Continuation of application No. 12/626,569, filed on Nov. 25, 2009, now Pat. No. 8,361,061, which is a continuation of application No. 11/197,849, filed on Aug. 5, 2005, now Pat. No. 7,625,372.

(60) Provisional application No. 60/656,036, filed on Feb. 23, 2005.

(51) Int. Cl.
| | |
|---|---|
| *A61B 18/08* | (2006.01) |
| *A61B 18/04* | (2006.01) |
| *A61B 18/14* | (2006.01) |

(52) U.S. Cl.  
USPC .................... 606/28; 606/41; 606/49

(58) Field of Classification Search  
USPC ........ 606/27–32, 41, 44; 607/96, 98–99, 101, 607/115–116  
See application file for complete search history.

(56) References Cited

U.S. PATENT DOCUMENTS

| | | | |
|---|---|---|---|
| 373,399 | A | 11/1887 | Hamilton |
| 452,220 | A | 5/1891 | Gunning |
| 833,759 | A | 10/1906 | Sourwine |
| 1,943,543 | A | 1/1934 | McFadden |
| 2,022,065 | A | 11/1935 | Wappler |
| 3,100,489 | A | 8/1963 | Gagley |

(Continued)

FOREIGN PATENT DOCUMENTS

| | | |
|---|---|---|
| CN | 1068525 C | 7/2001 |
| JP | 02-104348 | 4/1990 |
| WO | WO 98-09575 | 3/1998 |

OTHER PUBLICATIONS

Aaron, Electrofulguration for Varicose Veins, The Medical Letter on Drugs and Therapeutics, Jul. 12, 1968, vol. 10, No. 14, Issue 248, p. 54.

(Continued)

*Primary Examiner* — Ronald Hupczey, Jr.  
(74) *Attorney, Agent, or Firm* — Thomas M. Johnson, Esq.

(57) ABSTRACT

An energy delivering probe is used for thermally coagulating and/or constricting hollow anatomical structures (HAS) including, but not limited to, blood vessels such as perforator veins. The probe includes a shaft and an energy source.

15 Claims, 23 Drawing Sheets

(56) References Cited

U.S. PATENT DOCUMENTS

| | | | |
|---|---|---|---|
| 3,230,957 A | 1/1966 | Seifert | |
| 3,301,258 A * | 1/1967 | Werner et al. | 606/50 |
| 3,313,293 A | 4/1967 | Chesebrough et al. | |
| 3,920,021 A | 11/1975 | Hiltebrandt | |
| 4,481,953 A | 11/1984 | Gold et al. | |
| 4,532,924 A | 8/1985 | Auth et al. | |
| 4,548,207 A | 10/1985 | Reimels | |
| 4,561,445 A | 12/1985 | Berke et al. | |
| 4,643,186 A | 2/1987 | Rosen et al. | |
| 4,674,499 A | 6/1987 | Pao | |
| 4,682,596 A | 7/1987 | Bales et al. | |
| 4,765,331 A | 8/1988 | Petruzzi et al. | |
| 4,832,051 A | 5/1989 | Jarvik et al. | |
| 4,966,597 A | 10/1990 | Cosman | |
| 4,998,933 A | 3/1991 | Eggers et al. | |
| 5,122,137 A | 6/1992 | Lennox | |
| 5,281,216 A | 1/1994 | Klicek | |
| 5,281,218 A | 1/1994 | Imran | |
| 5,334,193 A | 8/1994 | Nardella | |
| 5,403,311 A * | 4/1995 | Abele et al. | 606/49 |
| 5,437,664 A * | 8/1995 | Cohen et al. | 606/42 |
| 5,556,396 A | 9/1996 | Cohen et al. | |
| 5,562,703 A | 10/1996 | Desai | |
| 5,630,426 A | 5/1997 | Eggers et al. | |
| 5,643,257 A | 7/1997 | Cohen et al. | |
| 5,658,282 A | 8/1997 | Daw et al. | |
| 5,695,495 A | 12/1997 | Ellman et al. | |
| 5,700,262 A | 12/1997 | Acosta et al. | |
| 5,709,224 A | 1/1998 | Behl et al. | |
| 5,734,903 A | 3/1998 | Saulpaugh et al. | |
| 5,743,903 A | 4/1998 | Stern et al. | |
| 5,752,951 A | 5/1998 | Yanik | |
| 5,766,167 A | 6/1998 | Eggers et al. | |
| 5,810,802 A | 9/1998 | Panescu et al. | |
| 5,868,744 A * | 2/1999 | Willmen | 606/50 |
| 5,893,849 A | 4/1999 | Weaver | |
| 5,897,553 A | 4/1999 | Mulier et al. | |
| 5,925,045 A | 7/1999 | Reimels et al. | |
| 5,928,159 A | 7/1999 | Eggers et al. | |
| 5,954,715 A | 9/1999 | Harrington et al. | |
| 5,964,754 A | 10/1999 | Osypka | |
| 5,976,131 A | 11/1999 | Guglielmi et al. | |
| 6,003,397 A | 12/1999 | Yasuhira | |
| 6,004,319 A | 12/1999 | Goble et al. | |
| 6,014,589 A | 1/2000 | Farley et al. | |
| 6,030,382 A | 2/2000 | Fleischman et al. | |
| 6,033,397 A | 3/2000 | Laufer et al. | |
| 6,033,398 A | 3/2000 | Farley et al. | |
| 6,036,687 A | 3/2000 | Laufer et al. | |
| 6,036,689 A | 3/2000 | Tu et al. | |
| 6,041,679 A | 3/2000 | Slater et al. | |
| 6,042,590 A | 3/2000 | Sporri et al. | |
| 6,066,136 A | 5/2000 | Geistert | |
| 6,071,277 A | 6/2000 | Farley et al. | |
| 6,077,261 A | 6/2000 | Behl et al. | |
| 6,090,104 A | 7/2000 | Webster, Jr. | |
| 6,106,524 A | 8/2000 | Eggers et al. | |
| 6,113,596 A | 9/2000 | Hooven et al. | |
| 6,123,702 A | 9/2000 | Swanson et al. | |
| 6,135,997 A | 10/2000 | Laufer et al. | |
| 6,139,527 A | 10/2000 | Laufer et al. | |
| 6,152,899 A | 11/2000 | Farley et al. | |
| 6,156,032 A | 12/2000 | Lennox et al. | |
| 6,165,172 A | 12/2000 | Farley et al. | |
| 6,179,832 B1 | 1/2001 | Jones et al. | |
| 6,200,312 B1 | 3/2001 | Zikorus et al. | |
| 6,228,082 B1 * | 5/2001 | Baker et al. | 606/49 |
| 6,237,606 B1 | 5/2001 | Zikorus et al. | |
| 6,238,393 B1 | 5/2001 | Mulier et al. | |
| 6,258,084 B1 | 7/2001 | Goldman et al. | |
| 6,263,248 B1 | 7/2001 | Farley et al. | |
| 6,267,758 B1 | 7/2001 | Daw et al. | |
| 6,283,961 B1 | 9/2001 | Underwood et al. | |
| 6,293,944 B1 * | 9/2001 | Ellman et al. | 606/41 |
| 6,304,776 B1 | 10/2001 | Muntermann | |
| 6,312,428 B1 * | 11/2001 | Eggers et al. | 606/41 |
| 6,322,559 B1 | 11/2001 | Daulton et al. | |
| 6,332,880 B1 | 12/2001 | Yang et al. | |
| 6,346,102 B1 | 2/2002 | Harrington et al. | |
| 6,353,763 B1 | 3/2002 | George et al. | |
| 6,379,349 B1 | 4/2002 | Muller et al. | |
| 6,391,026 B1 | 5/2002 | Hung et al. | |
| 6,398,777 B1 * | 6/2002 | Navarro et al. | 606/7 |
| 6,398,780 B1 | 6/2002 | Farley et al. | |
| 6,401,719 B1 | 6/2002 | Farley et al. | |
| 6,451,011 B2 | 9/2002 | Tu | |
| 6,480,746 B1 | 11/2002 | Ingle et al. | |
| 6,488,679 B1 | 12/2002 | Swanson et al. | |
| 6,539,265 B2 | 3/2003 | Medhkour et al. | |
| 6,565,557 B1 * | 5/2003 | Sporri et al. | 606/30 |
| 6,587,731 B1 | 7/2003 | Ingle et al. | |
| 6,613,045 B1 | 9/2003 | Laufer et al. | |
| 6,638,273 B1 | 10/2003 | Farley et al. | |
| 6,669,672 B2 | 12/2003 | Wu | |
| 6,669,692 B1 | 12/2003 | Nelson et al. | |
| 6,682,526 B1 | 1/2004 | Parker et al. | |
| 6,689,126 B1 | 2/2004 | Farley et al. | |
| 6,712,840 B2 | 3/2004 | Sun | |
| 6,723,094 B1 | 4/2004 | Desinger | |
| 6,733,499 B2 | 5/2004 | Scheib | |
| 6,752,767 B2 | 6/2004 | Turovskiy et al. | |
| 6,752,803 B2 | 6/2004 | Goldman et al. | |
| 6,761,718 B2 | 7/2004 | Madsen | |
| 6,769,433 B2 | 8/2004 | Zikorus et al. | |
| 6,770,070 B1 | 8/2004 | Balbierz | |
| 6,969,388 B2 | 11/2005 | Goldman et al. | |
| 6,981,972 B1 | 1/2006 | Farley et al. | |
| 7,004,942 B2 | 2/2006 | Laird et al. | |
| 7,041,098 B2 | 5/2006 | Farley et al. | |
| 7,160,289 B2 | 1/2007 | Cohen | |
| 7,195,630 B2 | 3/2007 | Ciarrocca | |
| 7,517,349 B2 | 4/2009 | Truckai et al. | |
| 7,625,372 B2 | 12/2009 | Esch et al. | |
| 7,641,633 B2 | 1/2010 | Laufer et al. | |
| 7,824,408 B2 | 11/2010 | Mirizzi et al. | |
| 2001/0023365 A1 | 9/2001 | Medhkour et al. | |
| 2001/0041888 A1 | 11/2001 | Goldman et al. | |
| 2002/0072744 A1 | 6/2002 | Harrington et al. | |
| 2002/0128641 A1 | 9/2002 | Underwood et al. | |
| 2002/0143325 A1 | 10/2002 | Sampson et al. | |
| 2002/0148476 A1 | 10/2002 | Farley et al. | |
| 2003/0191512 A1 * | 10/2003 | Laufer et al. | 607/101 |
| 2004/0153053 A1 | 8/2004 | Ishikawa | |
| 2004/0176761 A1 | 9/2004 | Desinger | |
| 2005/0043761 A1 | 2/2005 | Connelly et al. | |
| 2005/0070894 A1 | 3/2005 | McClurken | |
| 2005/0234443 A1 | 10/2005 | Rioux et al. | |
| 2006/0030849 A1 | 2/2006 | Mirizzi et al. | |
| 2006/0189979 A1 | 8/2006 | Esch et al. | |
| 2006/0217692 A1 | 9/2006 | Neuberger | |
| 2008/0039829 A1 | 2/2008 | Goldman et al. | |
| 2008/0243076 A1 | 10/2008 | Goldan et al. | |
| 2009/0149909 A1 | 6/2009 | Ameri | |
| 2009/0281535 A1 | 11/2009 | Truckai et al. | |
| 2009/0312673 A1 | 12/2009 | Thapliyal et al. | |
| 2010/0152723 A1 | 6/2010 | Esch et al. | |
| 2011/0144642 A1 | 6/2011 | Mirizzi et al. | |

OTHER PUBLICATIONS

Brunelle et al., A Bipolar Electrode for Vascular Electrocoagulation with Alternating Current, Radiology, Oct. 1980, vol. 137, pp. 239-240.
Corbett, Phlebology 17:36-40 (2002).
Cragg et al., Endovascular Diathermic Vessel Occlusion, Diagnostic Radiology, 144:303-308, Jul. 1982.
Hejhal L., Firt P., Livora D.; Endovaskularni Elektrokoagulace Povrchnich Zilnich Mestku Dolnich Koncetin (Endovascular Electrocoagulation of Superficial Varices of the Lower Limbs); Rozhledy v chirurgli (Surgical Outlooks) 1959, vol. XXXVIII-6 (Translation Provided).
International Search Report for Application No. PCT-US2005-027924 (the PCT counterpart of the parent application) mailed Dec. 19, 2005.

(56) References Cited

OTHER PUBLICATIONS

International Search Report for related PCT Application No. PCT-US2010-061951 from International Searching Authority (EPO) mailed Jul. 20, 2011.

Kianifard et al., "Surgical technique and preliminary results of transluminal occlusion of perforator veins", in "Vascular Surgical Society of Great Britain and Ireland abstracts", British J. of Surgery 2002, vol. 89, pp. 507-526, at 508, 2002 Blackwell Science Ltd.

Official Action from Japanese Patent Office (JPO) for Application No. 2007-525036, dated Feb. 2, 2012.

Ogawa et al., Electrothrombosis as a Treatment of Cirsoid Angioma in the Face and Scalp and Varicosis of the Leg, Plastic and Reconstructive Surgery, vol. 3, Sep. 1982, pp. 310-311.

O'Reilly, A Technique of Diathermy Sclerosis of Varicose Veins, The Australian, New Zealand Journal of Surgery, vol. 51, No. 4, Aug. 1981, pp. 379-382.

O'Reilly, Endovenous Diathermy Sclerosis as a Unit of the Armamentarium for the Attack on Varicose Veins; The Medical Journal of Australia, Jun. 1, 1974, p. 900.

O'Reilly, Endovenous Diathermy Sclerosis of Varicose Veins, The Australian, New Zealand Journal of Surgery, vol. 47, No. 3, Jun. 1977, pp. 339-395.

The Whiteley Clinic, "How the Whiteley Clinic has changed Vein Surgery in the UK—1", retrieved from http:--www.pioneering-veins-surgery.co.uk-how-the-whiteley-clinic-changed-varicose-vein-surgery-in-the-uk.htm on Nov. 19, 2009.

Watts, Endovenous Diathermy Destruction of Internal Saphenous, British Medical Journal, Oct. 7, 1972, p. 53.

Whiteley et al. (2003) Venous Forum Abstracts, Phlebology 18:1, p. 52.

Written Opinion for related PCT Application No. PCT-US2010-061951 from International Searching Authority (EPO) mailed Jul. 20, 2011.

\* cited by examiner

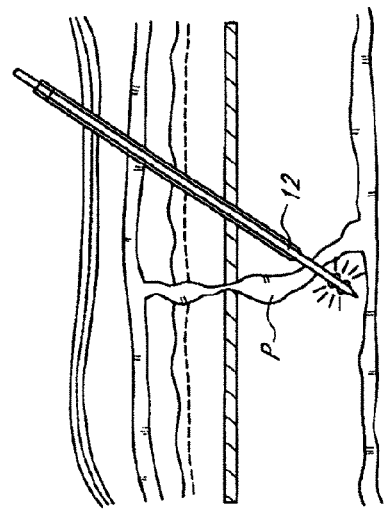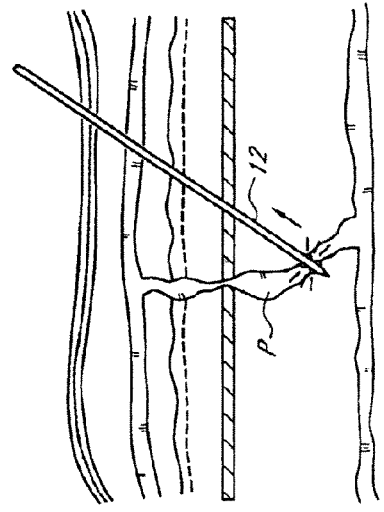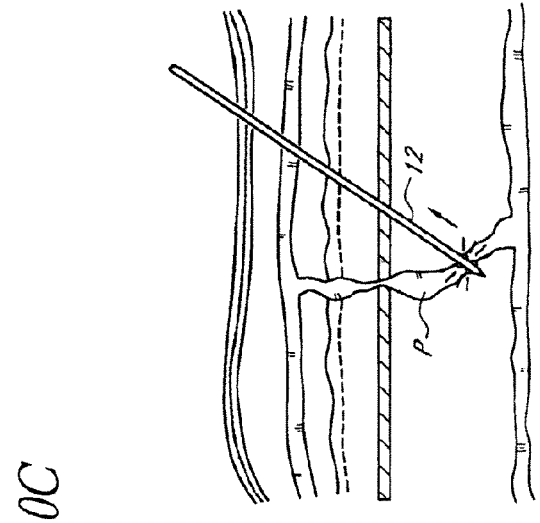
FIG. 10A
FIG. 10B
FIG. 10C
FIG. 10D

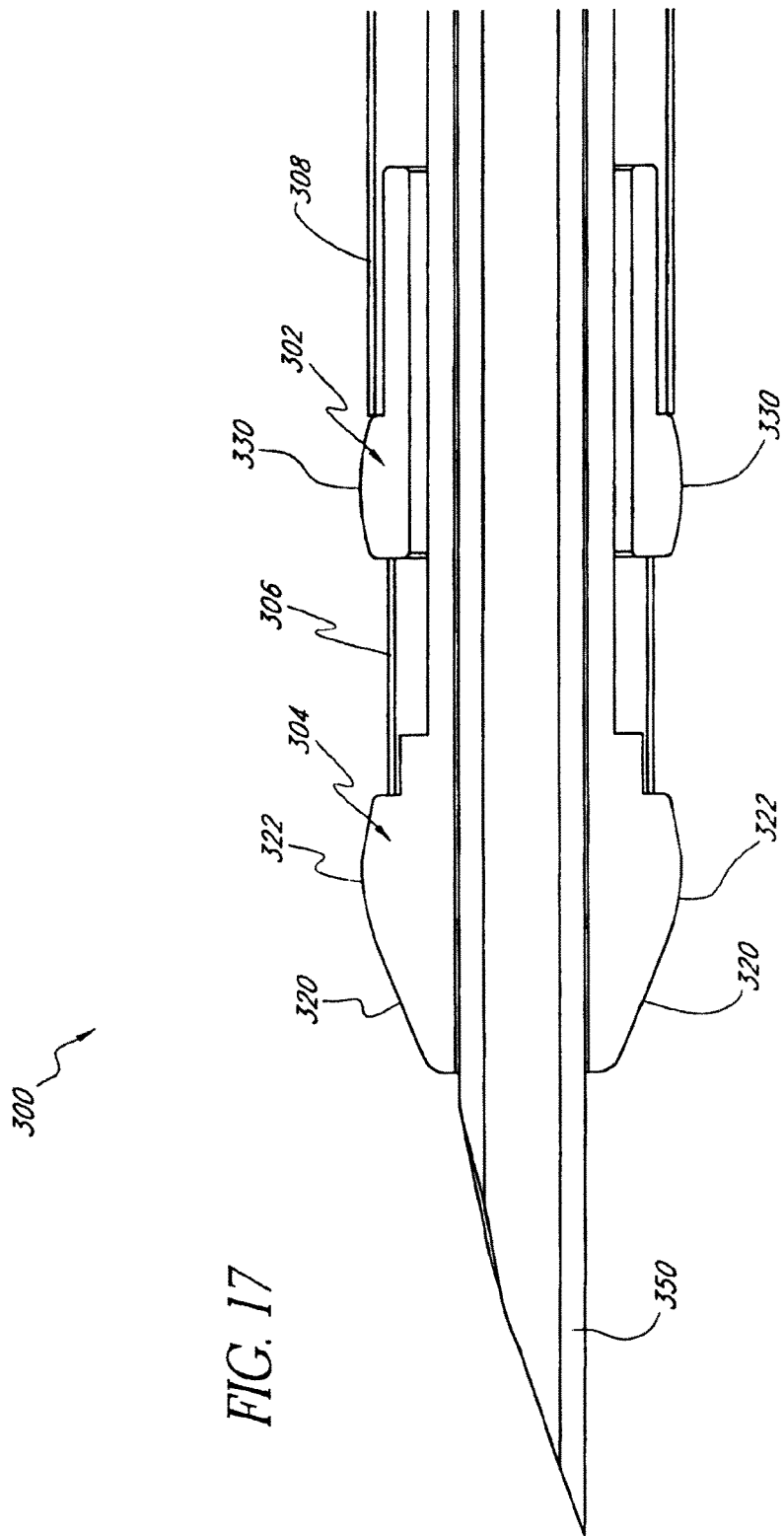

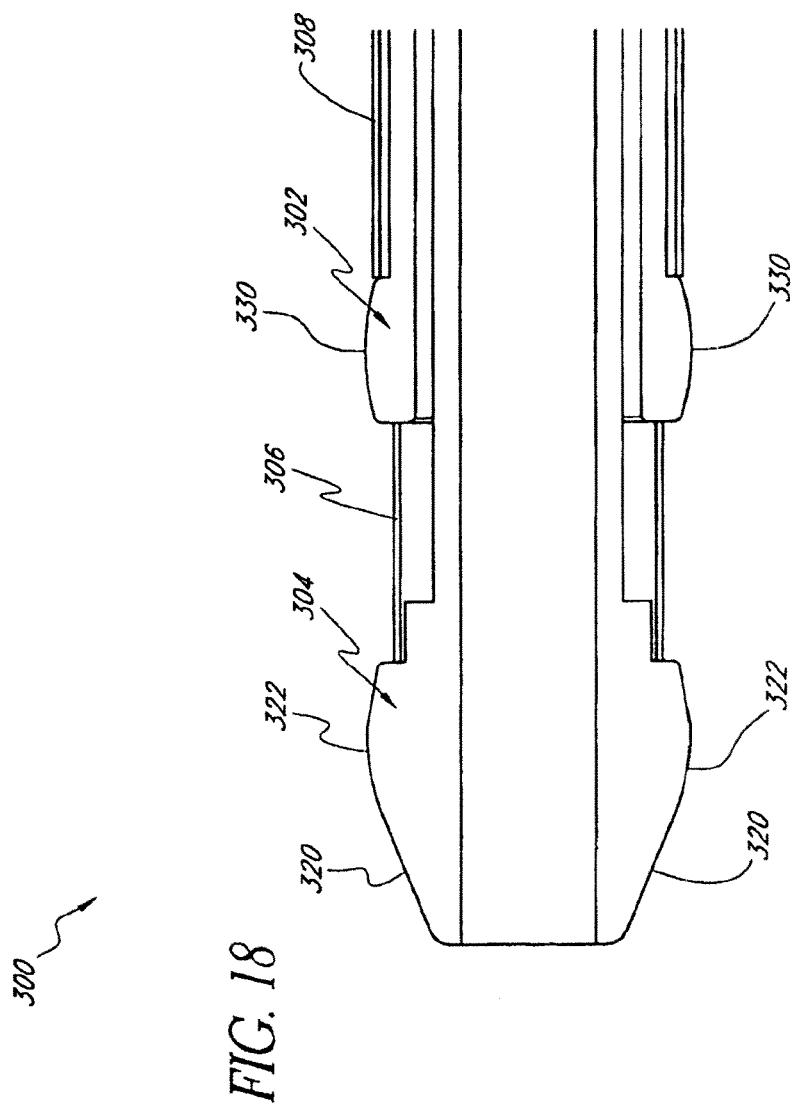

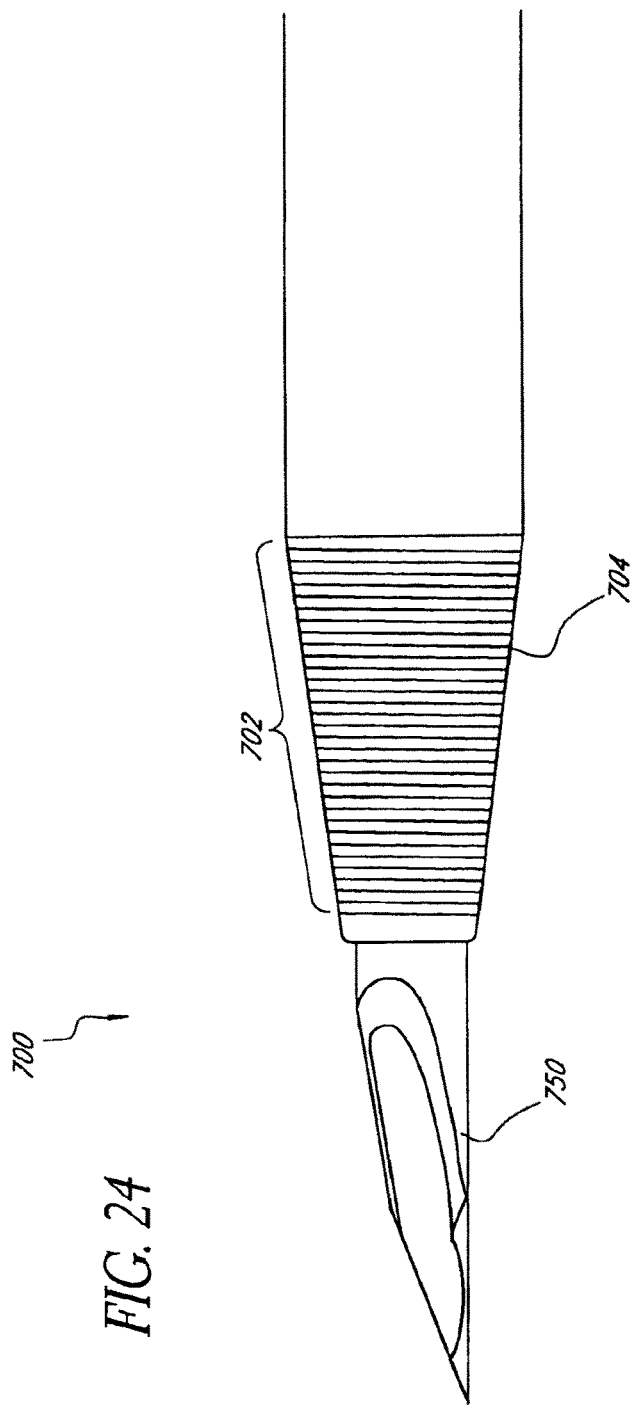

METHODS AND APPARATUS FOR COAGULATING AND/OR CONSTRICTING HOLLOW ANATOMICAL STRUCTURES

CROSS-REFERENCE TO RELATED APPLICATIONS

This Application is a continuation of U.S. application Ser. No. 12/626,569, filed Nov. 25, 2009, now U.S. Pat. No. 8,361,061, which is a continuation of U.S. application Ser. No. 11/197,849, filed Aug. 5, 2005, now U.S. Pat. No. 7,625,372, which claims priority under 35 U.S.C. 119(e) to U.S. Provisional Application No. 60/656,036 filed on Feb. 23, 2005, the entire disclosures of which are hereby incorporated by reference herein and made a part of this specification.

BACKGROUND

1. Field

The present disclosure relates generally to medical methods and apparatus. More particularly, the disclosure relates to the design and use of energy delivering probes for thermally coagulating and/or constricting hollow anatomical structures (HAS) including blood vessels such as the perforator veins which connect the superficial veins to the deep veins in the leg, truncal superficial veins of the leg (e.g., great saphenous vein, short saphenous vein, and the like), superficial tributary veins of the leg, internal spermatic veins (varicoceles), ovarian veins, gonadal veins, hemorrhoidal vessels, fallopian tubes, a-v malformations, a-v fistula side branches, esophageal varices, and the like. Additionally, the probes may be used for thermally coagulating tissue, such as cancerous breast or liver tissue. For purposes of illustration, apparatus and methods for use in treating perforator veins will typically be described.

2. Description of the Related Art

Perforator veins connect the deep venous system of a leg to the surface veins which lie closer to the skin. Normal or healthy perforator veins pass blood from the surface veins to the deep veins as part of the normal blood circulation. Incompetent perforator veins allow blood flow from the deep venous system to the surface veins, causing or contributing to problems, such as varicose veins, edema, skin and soft tissue changes, lipodermatosclerosis, chronic cellulites, venous ulcers, and the like.

Several procedures have been proposed for interruption of incompetent perforator veins. The "Linton" procedure requires a very long incision (knee to ankle) on the medial calf to expose the perforator veins. Individual veins may then be surgically dissected, ligated, and cut to prevent blood flow between the superficial and deep venous systems. A less invasive alternative has been developed by DePalma where individual incompetent perforator veins are identified along "Linton's Line" using ultrasound. Small incisions are then used to access the individual perforators for ligation and dissection. More recently, individual ligation and dissection of perforator veins has been performed using an endoscope inserted in the proximal calf.

Although generally effective, each of the above-described procedures requires surgical incisions followed by ligation and cutting of the veins. Thus, even at best, the procedures are traumatic to the patient and require significant surgical time. Moreover, the procedures are complex and often require a second surgeon to assist in the procedure.

For these reasons, it would be desirable to provide additional and improved techniques for disrupting incompetent perforator veins for the treatment of varicose veins, edema, skin and soft tissue changes, lipodermatosclerosis, chronic cellulites, venous ulcers, venous ulcers, and other conditions. Such procedures should preferably be minimally invasive, e.g., relying on an introducer sheath, cannula, catheter, trocar, or needle for gaining access to the perforator veins at the deep fascial plane. In particular, it would be desirable if the methods required few or no incisions, could be performed under a local anesthetic, would reduce post-operative healing time, as well as morbidity and complication rates, and would require only a single surgeon. In addition, it would be desirable to provide apparatus and methods which are useful for performing procedures on other tissues and hollow anatomical structures in addition to perforator veins. At least some of these objectives will be met by the disclosure described herein below.

SUMMARY

The present disclosure provides both apparatus and methods for coagulating and/or constricting a hollow anatomical structure (HAS) in order to inhibit or stop fluid flow therethrough. By "constricting," it is meant that a portion of the lumen of the treated HAS is reduced in size so that fluid flow therethrough is either reduced or stopped entirely. Usually, constriction will result from endothelial denudation, a combination of edema and swelling associated with cellular thermal injury, and denaturation and contraction of the collagenous tissues, leading to a fibrotic occlusion of the HAS so that fluid flow is reduced or stopped entirely. In other cases, constriction could result from direct fusion or welding of the walls together, typically when pressure and/or energy are applied externally to the HAS. In either case, some portions of the lumen may remain open allowing fluid flow at a greatly reduced rate. The constriction may thus occur as a result of contraction of the collagenous tissue in the HAS, or may alternately occur as a result of direct fusion or welding of the walls together induced by heating of that tissue and/or surrounding tissue. Such heating may occur as a result of the application of energy directly to the walls of the HAS and/or to the tissue surrounding the HAS. Although the disclosure will describe delivering RF energy from the electrode(s) it is understood that other forms of energy such as microwave, ultrasound, lower frequency electrical energy, direct current, circulating heated fluid, fiber optics with radiant light, and lasers, as well as thermal energy generated from a resistive coil or curie point element may be used as well. In the case of RF energy, the energy will typically be applied at a power level in the range from 0.1 W to 300 W, typically at a frequency in the range from 100 KHz to 1 MHz and for a time in the range from 1 second to 5 minutes, although for longer regions, the treatment time could be 10 minutes or longer.

While the apparatus and methods of the disclosure will be particularly suitable for constricting incompetent perforator veins for the treatment of varicose veins, venous ulcers, or the like, they will also be suitable for treating other venous structures, such as the saphenous veins for the treatment of venous reflux, and other conditions. In other cases, the apparatus and methods may be suitable for treatment of arterial and other hollow anatomical structures as well. In other cases, the apparatus and methods may be suitable for treatment of tissues such as cancerous breast or liver tissue.

The methods of the present disclosure may be performed with a wide variety of apparatus which are adapted to position electrode structures adjacent to or within the HAS to be constricted, typically a perforator vein at a location beneath the fascial layer. The apparatus will generally include a shaft having the electrode structure at or near its distal end. The electrode structure may comprise one or more electrode(s) energized at a common polarity for use in "monopolar" protocols. Alternatively the electrode structure may comprise at least two electrically isolated electrodes for performing bipolar protocols. The electrode shaft may be rigid, flexible, or have regions of varying rigidity and/or flexibility. Often, the apparatus shaft will be used in combination with an introducer sheath, cannula, or catheter where the shaft will be introduced through a lumen thereof. For example, the apparatus may be introduced through the working channel of an endoscope which acts as a delivery sheath or cannula. Alternatively or additionally, the shaft itself may comprise one or more lumens, and such lumen(s) may be adapted to receive a needle or trocar to facilitate direct or "self-penetrating" introduction of the shaft or to advance the shaft over a guidewire through tissue to the target treatment site. As a third alternative, the shaft may have an integral or fixed sharpened distal tip in order to allow direct or "self-penetrating" introduction of the shaft through tissue to the target treatment site. The latter two approaches will generally require that at least a portion of the shaft be rigid in order to allow for pushability, but it would also be possible to provide for temporary placement of a rod or other stiffening element within or around an otherwise flexible shaft while it is being forwardly advanced through tissue to the target treatment site.

Thus, the apparatus of the present disclosure may be introduced to the target treatment site in a variety of ways, including direct or "self-penetrating" introduction where the shaft has a sharpened distal tip, either permanently affixed or removably placed in a lumen of the shaft, e.g. using a needle or trocar. Alternatively, the shaft carrying the electrodes may be introduced through the lumen of a separate introducer sheath, cannula, or catheter which has been previously introduced using conventional techniques. Third, the shaft can be introduced over a guidewire which has been previously introduced, typically using a needle for conventional guidewire placement. Other introduction protocols, including combinations of the three just described, may also be used. Furthermore, endoscopic introduction as well as endoscopically guided introduction of the apparatus may also be used.

The treatment protocols of the present disclosure may rely on endovascular treatment, extravascular treatment, or combinations thereof. By "endovascular," it is meant that one or more of the treatment electrodes will be introduced into the lumen of the HAS being constricted. The electrodes may be introduced and left at a treatment location immediately adjacent to the entry penetration through the HAS wall. Alternatively, particularly when using flexible shafts and guidewires, the electrodes may be advanced intraluminally to a treatment location spaced some distance from the entry penetration through the HAS wall. By "extravascular," it is meant that the treatment electrodes are placed adjacent or near to the outside wall of the HAS being treated. More simply, the electrode structure may be introduced to such a location outside of the HAS wall, and the treatment initiated by delivering the treatment energy. Alternatively, the electrodes may be pinned on the side of the HAS wall using a sharpened tip or trocar associated with the apparatus shaft. The combinations of these approaches may also be used, for example where a first electrode is passed to a posterior side of the HAS while a second electrode remains on the anterior side.

In one aspect, a bipolar electrode probe comprises a shaft having a proximal end and a distal end, a generally spherical or toroidal first electrode disposed near the distal end of the shaft, a second electrode spaced axially from the first electrode, and an electrical connector near the proximal end of the shaft for connecting the first and second electrodes to opposite poles of an electrosurgical power supply. By generally "spherical or toroidal," it is meant that the electrode will have an outer, exposed surface which protrudes radially from a cylindrical wall or section of the shaft. The outer surface will usually be axially symmetrical and will be curved in a plane passing axially through the shaft. The curve will preferably be smooth, but will not necessarily have a constant radius. The radius will usually vary with a range from 0.5 to 10 times the shaft diameter.

In the preferred embodiments, the bipolar electrode probes will include only first and second electrodes. There will be no additional electrodes spaced axially from the first and second electrodes. In some cases, however, it may be desirable to form either the first or second electrodes in multiple segments arranged either axially or circumferentially, but such segments will always be commonly connected to a pole of the power supply and will be intended to act together as a single electrode surface.

In other specific embodiments, the second electrode structure will also be a generally spherical or toroidal electrode. In cases where both the first and second electrodes are spherical or toroidal, the more proximal of the two electrodes may have a less curved surface than the more distal of the electrodes. In some cases, the more proximal electrode may have a generally tapered, curved surface which becomes smaller in the distal direction. In other cases, the more distal electrode may have a taper in the distal direction providing an entry angle and transition to the electrode to ease advancing of the probe through tissue and/or through the wall of a hollow anatomical structure.

The spherical or toroidal electrodes will have a diameter in a range from 1 mm to 5 mm, preferably from 1 mm to 3 mm, typically being about 2 mm. The particular diameter chosen will depend on the selected method of access, where smaller diameter electrodes will require smaller access holes or incisions. The electrodes will be spaced-apart axially by a distance in the range from about 1 mm to 5 mm, preferably by about 1.5 mm (measured axially from inner edge to inner edge).

The shaft may be flexible or rigid and will preferably have at least a single central lumen extending from the proximal end to the distal end. The bipolar electrode structure may further comprise a trocar having a sharpened distal end disposed in one of the central or other lumens of the shaft so that the sharpened end extends distally beyond the shaft, typically by distance in the range from 1 mm to 10 mm. The trocar will preferably be removable, although in other embodiments described below, a trocar may be fixed to the shaft and define a distal-most electrode surface. In all cases, the trocar can be solid or flexible, but will preferably have an axial lumen to optionally permit introduction over a guidewire or delivery of fluid to the treatment site.

The trocar lumen can also provide for blood "flashback" indicating when the trocar has entered the HAS being treated.

In embodiments intended for direct introduction through tissue with a trocar or other sharpened distal tip, the shaft and/or the trocar will preferably be rigid to facilitate advancement. In other cases, where the electrode probe is intended for introduction over a guidewire, the shaft will usually be flexible. In the case of such flexible shafts, a sliding external sheath or cannula may be provided over the exterior in order to enhance stiffness to assist in insertion. Alternatively, in the case of flexible shaft devices, an internal stiffening member may be provided. Said stiffening member may be comprised of polymeric materials including PEEK, metals including stainless steel, composite structures including braided polyimide, and the like.

In a specific embodiment, the bipolar probe has a sharpened distal end that extends distally from the first electrode. The sharpened distal end may be formed as a trocar received within a central lumen of the shaft, usually being fixed in the shaft but optionally being removable and replaceable. Alternatively, the sharpened distal tip may be formed as a separate component and attached at the distal end of the shaft. The sharpened distal end is preferably electrically active and defines at least a portion of the electrode, preferably being formed as a cylindrical tube having a diameter in the range from about 0.5 mm to about 1 mm, and a length in the range from about 1.5 mm to 5 mm. The proximal end of the sharpened distal electrode and the distal end of the first electrode will preferably be spaced-apart by a distance in the range from 1 mm to 5 mm, preferably by about 1.5 mm. In some cases, the space between the electrode may be tapered in the distal direction providing an entry angle and transition to the electrode to ease advancing of the probe through tissue and/or through the wall of a hallow anatomical structure. The shaft will preferably have a lumen therethrough, including through the sharpened distal end, in order to permit the detection of flashback upon HAS entry, optional introduction over a guidewire and/or the delivery of saline or other fluids during a procedure.

In all of the above embodiments, at least one temperature sensor may be disposed on the probe, typically being on or near one or more of the electrodes. In the specific examples, at least one temperature sensor may be placed on a spherical or toroidal electrode. The temperature sensors will be suitable for connection to the external power supply to allow for monitoring and optional control of the temperature during the treatment.

In another aspect, a method for constricting a target HAS comprises percutaneously introducing a distal end of a probe to a location near the HAS and delivering energy into the target HAS to constrict the target region of the HAS. The probe may be introduced by advancing a sharpened distal end thereof through tissue directly to the target region, by positioning a sheath through tissue to the target region and advancing the probe through the sheath, or by positioning a guidewire through a needle, removing the needle, and advancing the probe over the guidewire to the location near the target HAS. Other combinations of these approaches may also be possible.

In some cases, it will be preferable to image the target location, such as the HAS and surrounding tissue while the probe is being introduced. Usually, color duplex or other ultrasonic imaging will be sufficient, although other imaging, such as fluoroscopic, would be possible. As a third alternative, the target location may be endoscopically viewed while the probe is being introduced, e.g., through a working channel of an endoscope.

The electrodes may be positioned in a variety of relationships to the HAS being treated. For example, the electrodes may be positioned extravascularly, typically on one side of the HAS, usually within 4 mm and preferably directly adjacent to the exterior of the HAS wall, while energy is being delivered. Alternatively, one or both electrodes may be positioned endovascularly where the electrode(s) are located within a lumen of the HAS when energy is delivered.

In a specific embodiment, an electrode having a sharpened end is penetrated through the HAS while an exterior surface of the HAS is engaged by a spherical or toroidal electrode on the probe. The HAS may be collapsed by pressure from the spherical or toroidal electrode so that the simultaneous application of pressure and heat will cause constriction of the HAS.

In other alternative protocols, either or both of the electrodes, preferably spherical or toroidal electrodes, may be passed entirely through the target HAS and thereafter drawn backwardly against the HAS wall and optionally through the HAS wall while applying energy.

In some preferred aspects, the temperature will be monitored near at least one of the electrodes, allowing monitoring and/or control of the HAS constriction. For example, the radiofrequency energy may be delivered at from 0.1 W to 300 W to obtain a monitored temperature in the range from 70° C. to 100° C. for a time sufficient to achieve HAS constriction.

In further preferred aspects of some methods, saline or other physiologically acceptable fluid will be delivered to the region being treated while the radiofrequency energy is being delivered. Preferably, the fluid will be delivered through a lumen in the probe itself.

In another aspect, a method for constricting a perforator vein comprises introducing at least one electrode to a location adjacent to or within the perforator vein and delivering energy through the electrode to constrict the lumen of the perforator vein.

In yet another aspect, an electrode probe comprises a shaft having a proximal end and a distal end, a generally spherical or toroidal first electrode disposed near the distal end of the shaft, and a second electrode spaced axially from the first electrode.

Another aspect is a probe with a proximal end and distal end for use in treating a hollow anatomical structure. Preferably, the probe has at least one energy emitting element located near its distal end, and the perimeter of this element increases as the element extends proximally. The probe may also have a sharp tip at its distal end that is configured to puncture body tissue as it is urged against the tissue.

Another aspect is an energy-emitting probe for use in treating a hollow anatomical structure comprising a shaft having a proximal end and distal end. Preferably, there is at least one energy emitting element located near the distal end of the shaft. The element may have an outer surface tapering outward as the element extends proximally, or a portion of the element may be cylindrical. Preferably, the probe also comprises a sharp tip at its distal end that is configured to puncture body tissue as it is urged against the tissue.

In another aspect, a method for treating body tissue with an energy-emitting probe comprises puncturing the body tissue with a sharp distal end of the probe and advancing the shaft of the probe distally into the tissue. Preferably, the method further comprises inserting an energy emitting element having tapered edges into the body tissue, the tapered edges easing insertion of the element into the tissue.

BRIEF DESCRIPTION OF THE DRAWINGS

FIGS. 10A-10E illustrate the use of the probe of FIG. 1 for performing a third exemplary procedure according to the principles of the disclosure.

FIGS. 17 and 18 illustrate an electrode configuration suitable for use with various embodiments of the electrode probe disclosed herein.

FIG. 24 illustrates a resistive-heater tip usable in place of, or in addition to, the electrode(s) of any of the various probes disclosed herein.

FIGS. 17 through 23 are drawn to scale.

DETAILED DESCRIPTION OF THE PREFERRED EMBODIMENT

Figure 1:
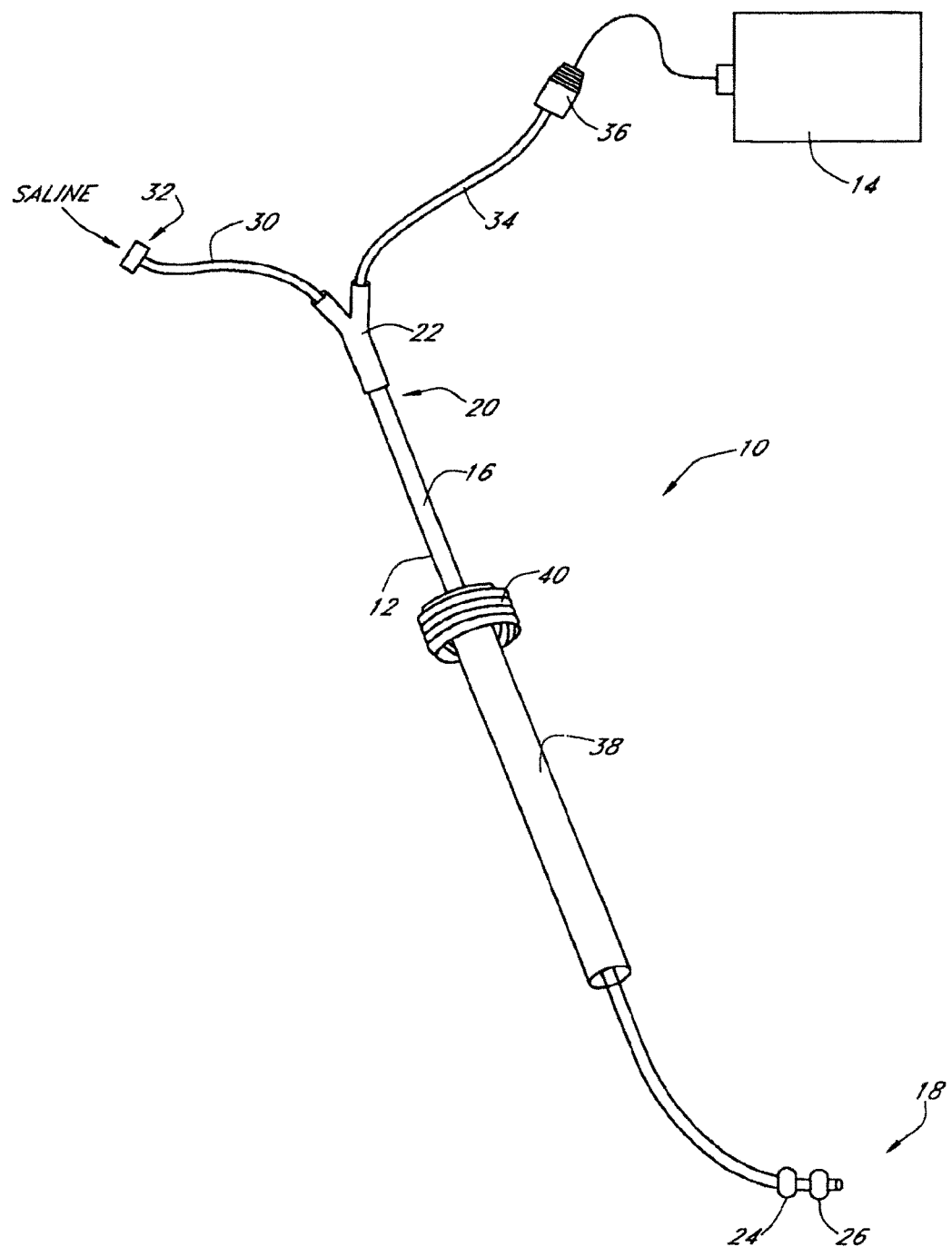
FIG. 1 illustrates a system constructed in accordance with principles of the disclosure including a probe and a radiofrequency electrosurgical power supply.

Referring to FIG. 1, a first exemplary system 10 constructed in accordance with principles of the disclosure comprises a bipolar electrode probe 12 and a radiofrequency (RF) electrosurgical power supply 14. A bipolar electrode probe 12 comprises a flexible shaft 16 having a distal end 18 and a proximal end 20 having a Y-shaped connector hub 22 attached thereto. A first electrode 24 and second electrode 26 are mounted on the shaft 16 near the distal end 18. The shaft 16 has a central lumen which extends over its entire length (from the proximal end to the distal tip), and the lumen may be connected, typically via a luer connector (now shown) through a flexible line 30 having a luer or other connector hub 32 at its other end which can be connected to a source of infusion fluid, typically saline. The electrodes 24 and 26 may be connected to the radiofrequency electrosurgical power supply 14 through a cable 34 and connector 36. The connections to the electrodes 24 and 26 are isolated so that the two electrodes may be connected to opposite poles of the power supply 14, in the case of a bipolar configuration.

Optionally, an external sheath 38, typically in the form of a rigid metal or other cannula, is slidably received over the exterior of the flexible shaft 16. The sheath provides external stiffening of the flexible shaft 16 when desired. The sheath may include a handle or grip 40 near a proximal end thereof to facilitate its manipulation. Additionally, the sheath 38 may be sharpened at its distal end to allow for improved tissue penetration.

The external sheath 38 may allow selective stiffening of an otherwise flexible shaft 16. Typically, during access, the sheath 38 will be placed in a forwardly advanced position to provide a rigid structure which is more controllable during subcutaneous manipulation and advancement over a guidewire or through a cannula where flexibility is not required and can even be a disadvantage. After positioning a distal end 18 of the shaft 16 at the desired treatment location, the external sheath 38 can be partially or fully withdrawn to expose a distal length of the flexible shaft 16 to allow further advancement into the HAS or to simply remove the rigid structure during treatment or while external compression is used to manipulate the device tip into contact with the HAS wall.

The first and second electrodes 24 and 26 are illustrated as generally spherical or toroidal electrodes, as defined above. The flexible body 16, which is typically formed from a polymer or other electrically insulating material, acts to isolate the electrodes and provide the desired axial spacing, also as discussed above. While the electrodes are illustrated as spherical or toroidal, a variety of other specific designs may used under different circumstances, as will be discussed below.

Figure 2:
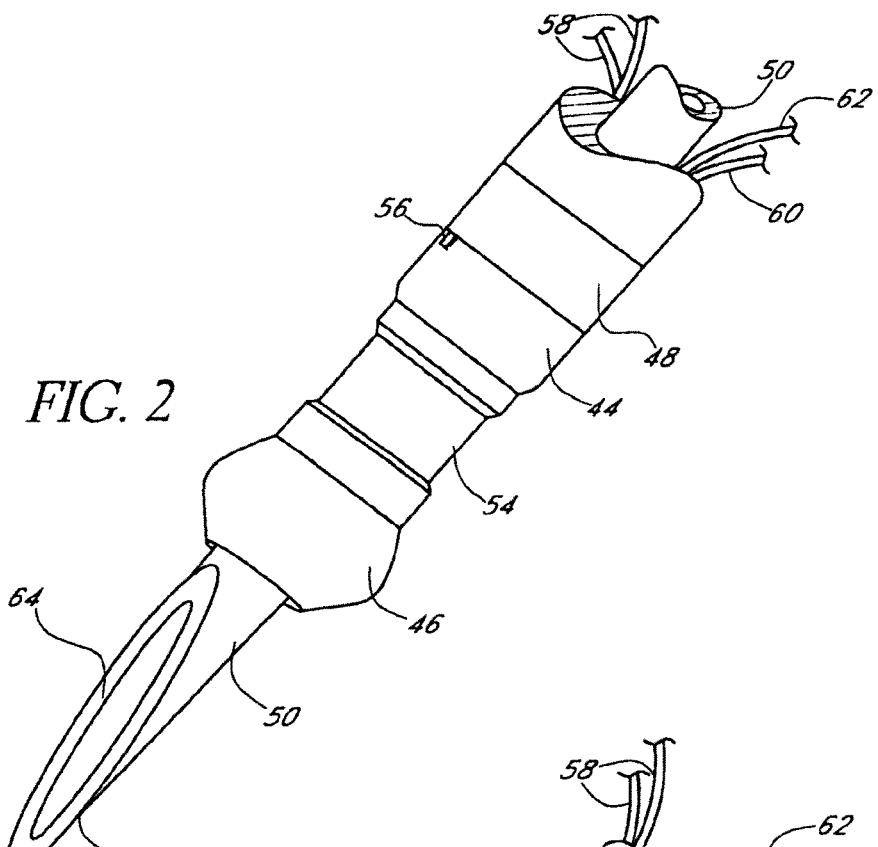
FIG. 2 illustrates a first exemplary distal tip of a probe constructed in accordance with principles of the disclosure.
Figure 3:
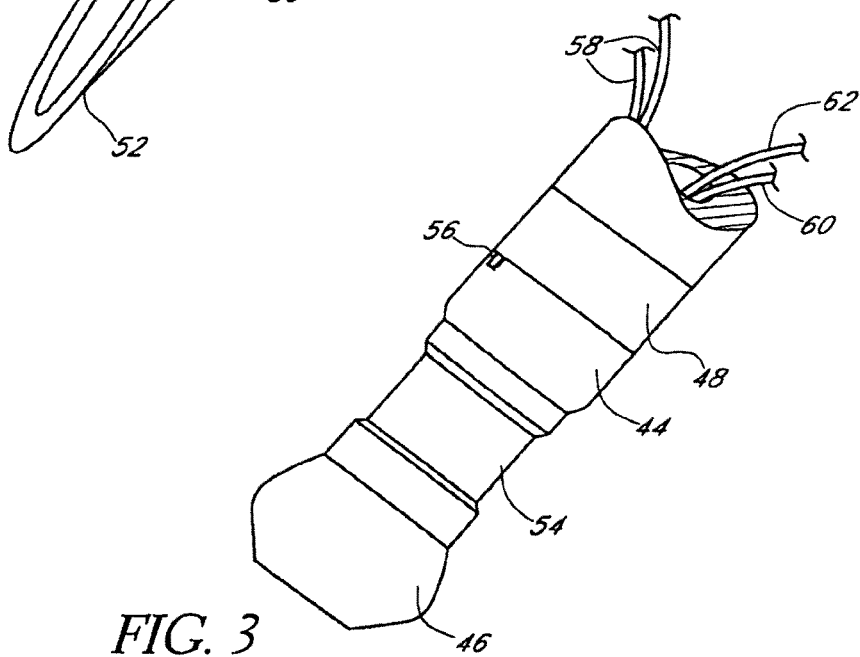
FIG. 3 illustrates the probe tip of FIG. 2, shown with an introducer trocar removed.

Referring now to FIGS. 2 and 3, a first specific electrode design comprising a first electrode 44 in the form of a ring which is typically toroidal with a very flat surface and a second electrode 46 which is generally spherical or toroidal, as defined above. The first and second electrodes are disposed at the distal end of a polymeric shaft or body 48, in a variety of ways. For the flexible shaft embodiment of FIGS. 1 through 3, as well as 4 discussed below, they can be attached through the center lumen of the shaft. Preferably, in embodiments that include spherical or toroidal electrodes, the opening formed in the center of the elements is approximately centered on the longitudinal axis of the shaft. Other embodiments are described below.

A trocar or needle 50 is received in the central lumen of the body 48. The trocar 50 has a sharpened distal end or tip 52 so that it may be introduced directly into solid tissue, for example for accessing a HAS in the procedures described below. Electrodes 44 and 46 are spaced-apart by a spacer 54 located therebetween and isolated by a polymeric tube (not shown) insulating the entire length under the proximal electrode 44. The trocar is preferably removable, leaving the structure illustrated in FIG. 3. At least one temperature sensor, typically a thermocouple or a thermistor 56, will be provided on or near either of the electrodes. As illustrated, it is at the proximal end of the first electrode 44. The temperature sensor is connected to the power supply through wires 58. The first and second electrodes are connected to a power supply through isolated wires 60 and 62. In other embodiments, the electrode(s) may run the entire length of the device, thus eliminating the need for separate connecting wires.

Usually, at least one of the probe body or shaft 48 and the trocar 50 will be rigid to facilitate advancement of the sharpened tip of trocar 50 through tissue. Usually, at least the trocar will be rigid since it will most often be composed of stainless steel or another metal. Often, the probe body 48 will also be rigid or stiffened by reinforcing elements.

The trocar 50 may have an internal lumen and a port or opening 64 at its distal end, typically to permit the detection of flashback upon HAS entry, optional introduction over a guidewire and/or the delivery of saline or other physiologically acceptable fluid to the treatment region during a procedure.

Figure 4:
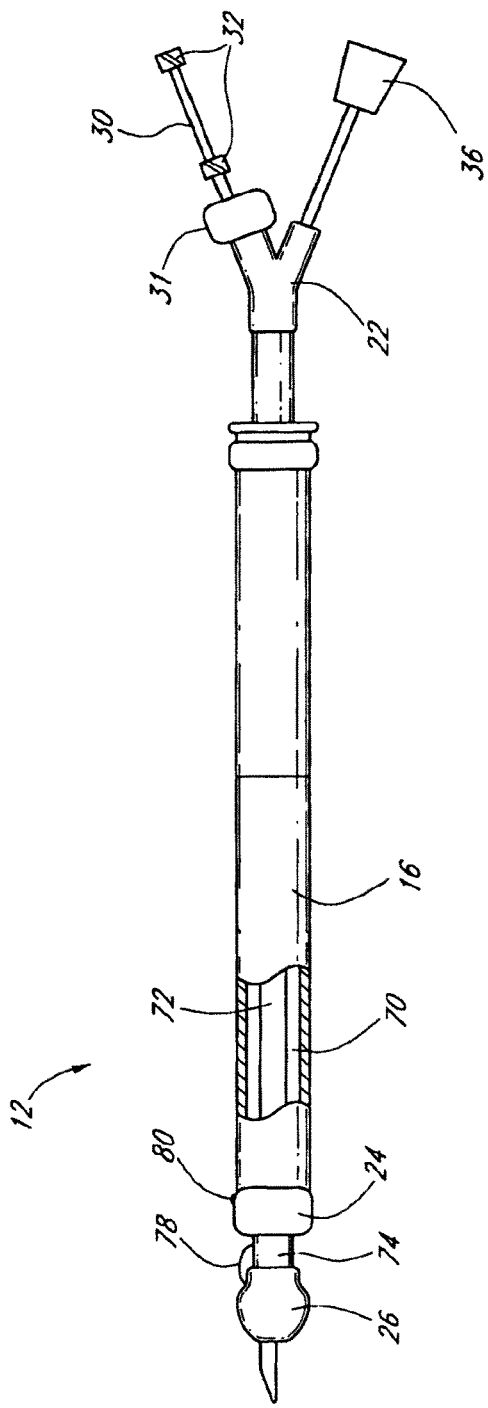
FIG. 4 illustrates a second exemplary probe constructed in accordance with principles of the disclosure, comprising a flexible shaft.

Construction of a particular embodiment of the electrosurgical probe 12 of FIG. 1 is shown in more detail in FIG. 4. The flexible body or shaft 16 has lumen 70 shown in a broken-away portion thereof. The lumen 70 carries a tube 72 which is connected to the second electrode 26. An insulating region 74 is provided between the second electrode 26 and the first electrode 24, and a wire 78 is connected to the second electrode and runs proximally through the probe and to the electrical connector 36. A second wire (not shown) is connected to the first electrode 24 and also runs proximally to the connector 36. Similarly, temperature sensor wires are connected to the thermocouple, thermistor, or other thermosensor 80 and run through the flexible body 16 to the connector 36. The inner shaft 72 is preferably formed from a structurally reinforced material such as braided polyimide, while the outer shaft may be formed from a polymeric extrusion such as thermoplastic polyester elastomers, polyimide, nylons, PEEK, polyether-block co-polyamide polymers, and the like. The connecting tube 30 may be formed from polyvinylchloride (PVC) or other suitable polymer and have a luer fitting 32 at both free ends. Tube 30 may be connected to the hub 22 by a luer 31.

Figure 5:
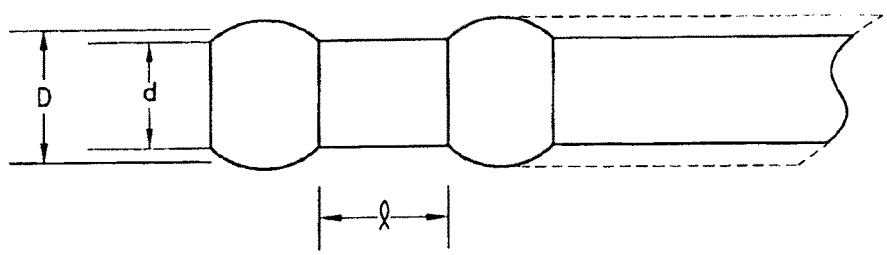
FIGS. 5 and 5A are schematic illustrations illustrating the dimensions of a first probe-tip construction according to the principles of the disclosure.
Figure 5A:
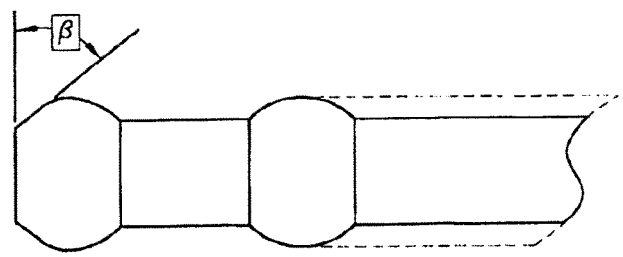

Referring now to FIG. 5, exemplary dimensions for embodiments which employ pairs of spherical or toroidal electrodes will be described. These spherical or toroidal electrodes will typically have a diameter D in a plane which is transversed to the axis of the catheter body in the range from 1 mm to 3 mm. The flexible probe body will have a diameter d which is smaller than that of the electrodes, typically being in the range from 0.5 mm to 2.5 mm. The distance l between the inner edges of the spherical electrodes will be in the range from 1 mm to 5 mm. As shown in FIG. 5A, the distal electrode may have a taper in the distal direction providing an entry angle β to the electrode improving the ability to advance the probe through tissue and/or through the wall of an HAS. The entry angle β of the spherical or toroidal electrode will be in the range from 0° to 90°, typically being in the range from 0° to 60°.

Figure 6:
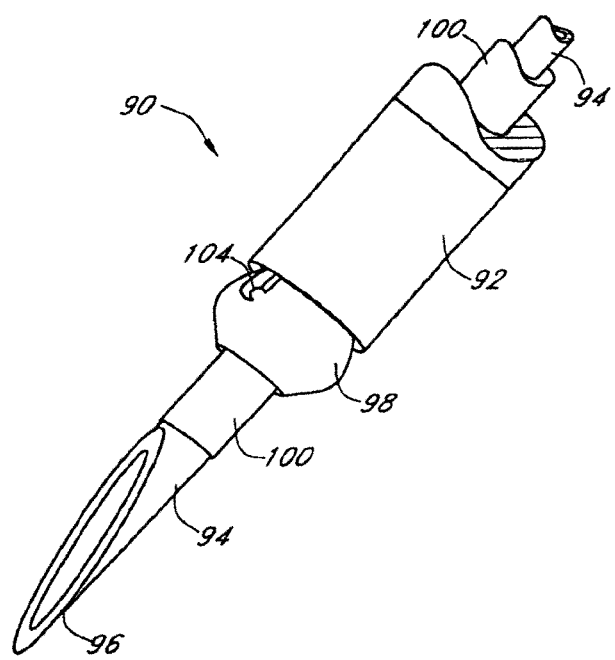
FIG. 6 illustrates a third exemplary probe constructed in accordance with principles of the disclosure.

Referring now to FIG. 6, a third embodiment of a bipolar electrode probe 90 constructed in accordance with principles of the disclosure is illustrated. Proximal portions of probe body 92 will be the same as for previously described embodiments. Probe body 92 may be rigid or flexible and will, as with prior embodiments, have a lumen therethrough. Within the lumen, a trocar 94 having a sharpened tip 96 will be removably received within the lumen. A first spherical or toroidal electrode 98 is integral or attached to the distal end of the probe body 92. The trocar 94 acts as the second electrode, and is insulated from the remaining components by a sleeve 100. The sleeve 100 may run the entire length of the device to provide insulation. The first electrode 98 may also run the entire length over the sleeve 100 and within the probe body 92 to provide for electrical connection back to a proximal hub (not shown). A thermocouple 104 or other temperature sensor may be connected through wires (not shown) which run the length of the probe. The apparatus of FIG. 6 can provide for the introduction of saline or other physiologically acceptable fluid through a multi-arm hub (not shown). The fluid can be delivered through the lumen running through the trocar 94 and/or through an annular space between the outer surface of sleeve 100 and the inner surface of the electrode 98.

Figure 7:
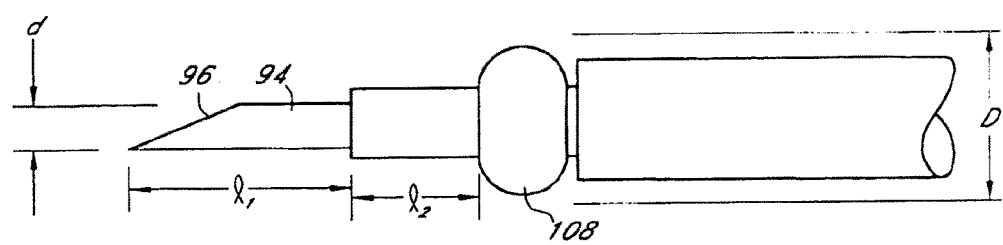
FIGS. 7, 7A, and 7B are schematic illustrations of alternate embodiments of the tip of the probe of FIG. 6 marked to show dimensions.
Figure 7A:
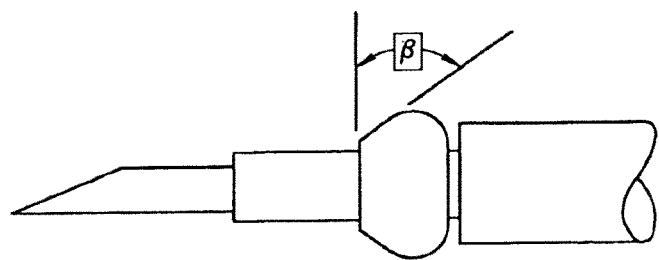
Figure 7B:
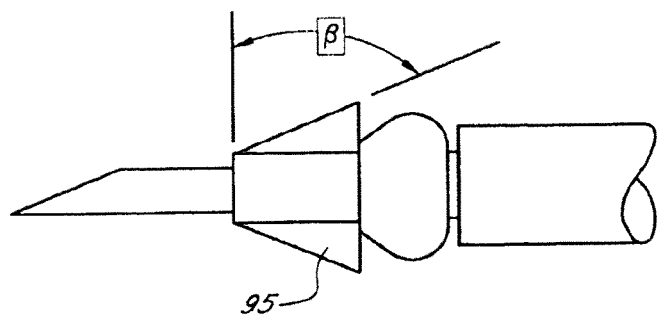

Typical dimensions for the distal probe end of FIG. 6 are shown in FIG. 7. The exposed portion of trocar 94 has a length l1 in the range from 1 mm to 10 mm, and a diameter d in the range from 0.5 mm to 1 mm. The proximal most end of the exposed trocar 94 is spaced apart from a spherical or toroidal electrode 108 by a distance l2 in the range from 1 mm to 5 mm. The diameter D of the spherical or toroidal electrode is generally the same as described above, typically being in the range from 1 mm to 3 mm. As shown in FIG. 7A, the generally spherical or toroidal electrode may have a taper in the distal direction providing an entry angle β to the electrode improving the ability to advance the probe through tissue and/or through the wall of an HAS. The entry angle β is generally the same as described above being in the range from 0° to 90°, typically being in the range from 0° to 60°. Optionally, as shown in FIG. 7B, the space between the electrodes may be tapered in the distal direction providing an entry angle β and transition element 95 improving the ability to advance the probe through tissue and/or through the wall of an HAS. The entry angle β is generally the same as described above being in the range from 0° to 90°, typically being in the range from 0° to 60°.

Figure 8C:
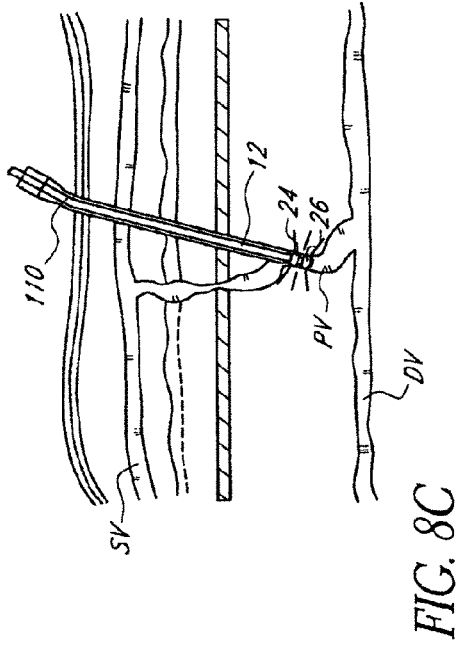
FIGS. 8A-8D illustrate use of the probe illustrated in FIG. 1 in performing a procedure according to a method.
Figure 8D:
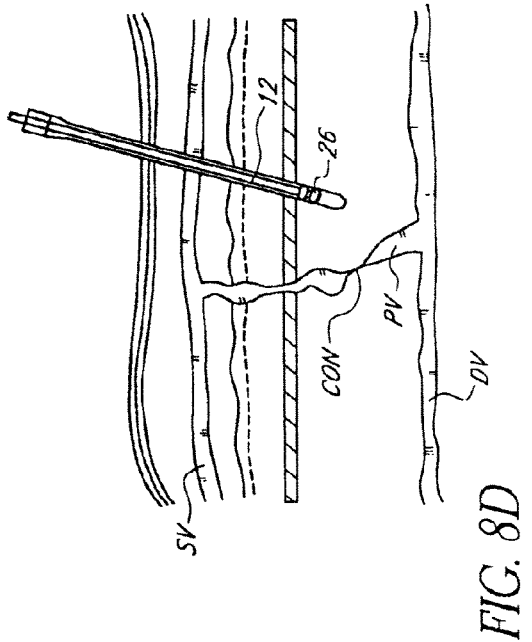
Figure 8A:
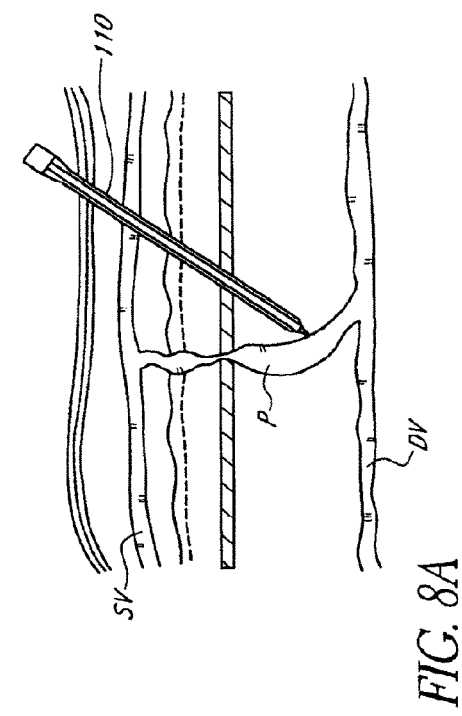
Figure 8B:
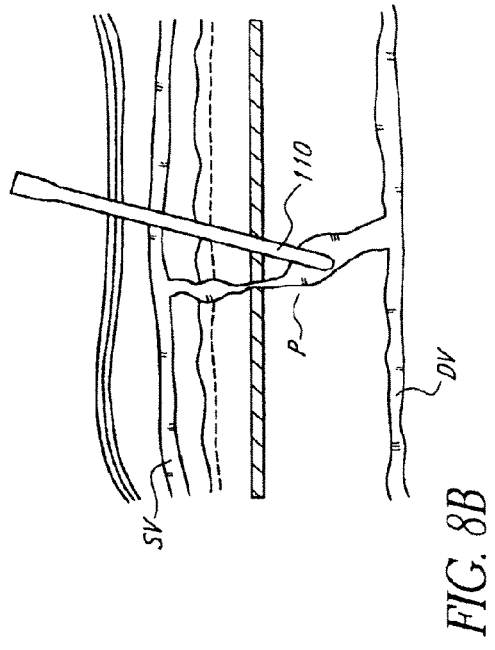

Referring now to FIGS. 8A-8D, use of the probe for performing constriction of a perforator vein P or other HAS is illustrated. While the use is described in connection with the rigid bipolar electrode probe 12, the method will generally apply to the other embodiments described herein. The perforator vein connects the deep venous system DV to the superficial venous system SV, as generally shown in each of the figures. Access to the perforator vein P or other HAS may be achieved with a conventional needle and cannula assembly 110, as illustrated. Alternatively, direct access may be achieved relying on the exposed trocar tip 52 or 96 (FIG. 2 or 6). As illustrated in FIGS. 8A-8D, cannula 110 is introduced through the skin to the target site, and a needle removed from the cannula, as shown in FIG. 8B. At this point, access to the interior of the perforator vein P or other HAS is provided. The probe 12 may be introduced through the cannula to a site within the perforator vein P or other HAS, as shown in FIG. 8C. Energy may then be applied through the electrodes 24 and 26 until a desired degree of constriction has been achieved. In the exemplary embodiments, bipolar RF energy will heat the tissue and/or HAS, the temperature will be monitored with a thermocouple on the probe, and the radiofrequency generator will modulate power to maintain the desired temperature. After a desired amount of treatment time, the treatment can be terminated and the probe and cannula removed, leaving a constricted region CON in the perforator vein PV as shown in FIG. 8D.

Figure 9A:
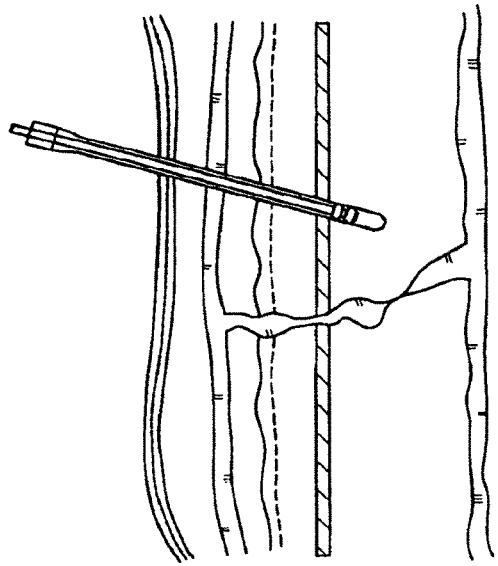
FIGS. 9A-9C illustrate the probe of FIG. 1 in performing a second exemplary procedure in accordance with principles of the disclosure.
Figure 9B:
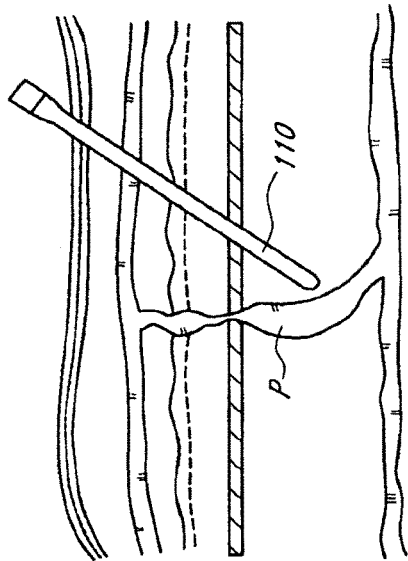
Figure 9C:
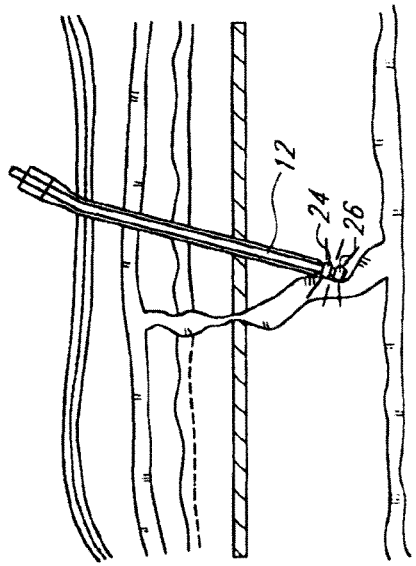

The treatment protocol illustrated in FIGS. 8A-8D, is generally referred to herein as endovascular, i.e., within the HAS. While the use is described in connection with the rigid bipolar electrode probe 12, the method will generally apply to the other embodiments described herein. Radiofrequency probe 12 may also be used to perform extravascular treatment, as illustrated in FIGS. 9A-9C. Access with the assembly 110 may be achieved as generally described before, except that the perforator vein P or other HAS is not necessarily penetrated. Alternatively, direct access may be achieved relying on the exposed trocar tip 52 or 96 (FIG. 2 or 6). As illustrated, the bipolar electrode probe 12 is introduced through the cannula 110 and the electrodes 24 and 26 are positioned adjacent the exterior of the vein or other HAS. The electrodes are energized and the tissue heated sufficiently to constrict the walls of the vein or other HAS, without any penetration, with the resulting constriction shown in FIG. 9C.

Figure 10E:
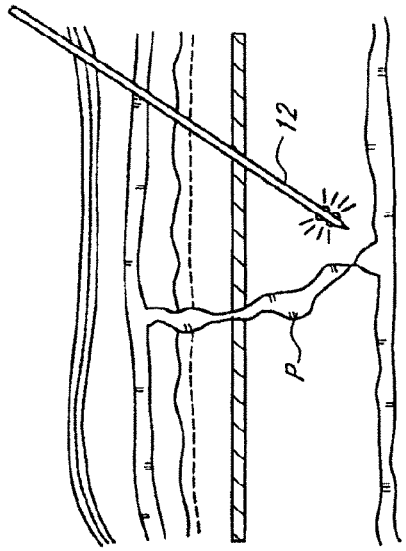

Referring now to FIGS. 10A-10E, a third protocol using the bipolar electrode probe 12 for constricting the perforator vein P or other HAS is illustrated. The needle and cannula 110 is introduced to fully penetrate the perforator vein P or other HAS so that the tip passes through the far side. The needle is removed and bipolar electric probe 12 introduced through a cannula, as shown generally in FIG. 10B. As illustrated, the probe 12 is rigid but it could also have a flexible shaft. While the use is described in connection with passing the probe through a cannula, this method could alternatively be performed by "directly" penetrating the vein with a probe having a needle or trocar in a central lumen thereof as in FIG. 2 or having a sharpened distal electrode being rigidly fixed to the probe as in FIG. 6. The electrodes on the probe 12 are then energized as the probe is drawn back to contact the far side of the vein or other HAS, as shown in FIG. 10C. The vein or other HAS is heated and collapsed as the probe 12 is continued to be drawn back through the HAS, as shown in FIG. 10D. Optionally, the cannula is completely removed by this point. As probe 12 is withdrawn, the perforator vein P or other HAS is constricted, as shown in FIG. 10E.

Figure 11A:
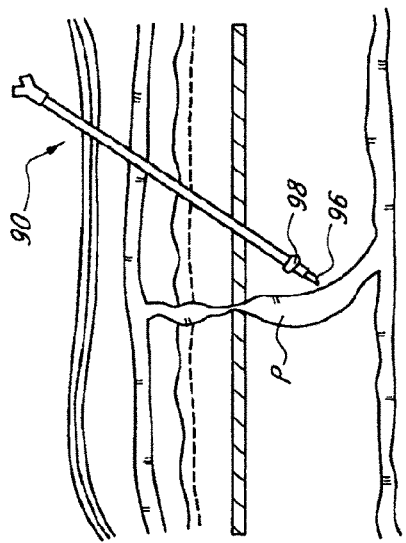
FIGS. 11A-11B illustrate the use of the probe of FIG. 6 for performing a fourth exemplary procedure according to principles of the disclosure.
Figure 11B:
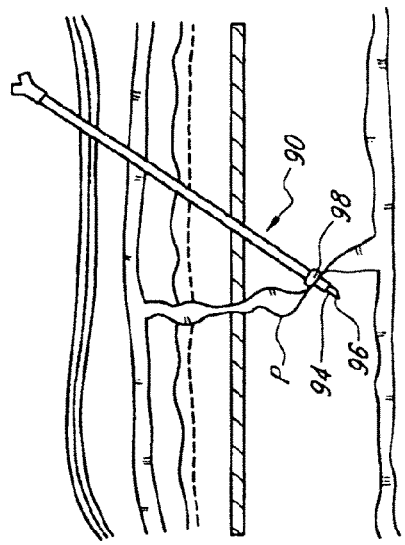

Referring now to FIGS. 11A and 11B, a fourth protocol of the bipolar electrode probe 90 of FIG. 6 for treating a perforator vein P or other HAS will be described. The probe 90 is introduced directly through tissue under ultrasonic guidance until the sharpened tip 96 contacts the exterior of the vein or other HAS. The surgeon then advances the sharpened tip 96 through the vein or other HAS so that the spherical or toroidal electrode 98 engages and collapses the vein or other HAS, as shown in FIG. 11B. The electrodes 94 and 98 are then energized to heat and constrict the walls of the vein or other HAS. As with all previous embodiments, the area may optionally be infused with saline or other physiologically acceptable fluid in order to enhance current flow, tissue heating, and HAS constriction. Hollow anatomical structure access may be confirmed by observation of flashback through a lumen of the system.

Figure 12A:
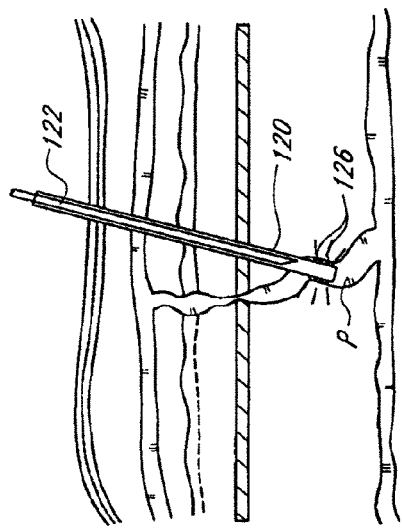
FIGS. 12A-12D illustrate the use of a trocar with a rigid probe having a pair of spaced-apart electrodes for endovascular treatment of a HAS in order to constrict the HAS in accordance with the principles of the disclosure.
Figure 12C:
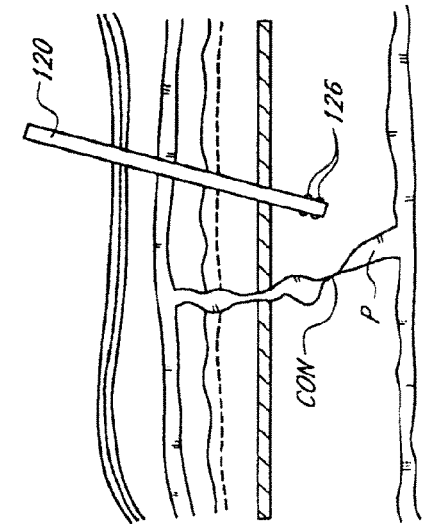
Figure 12B:
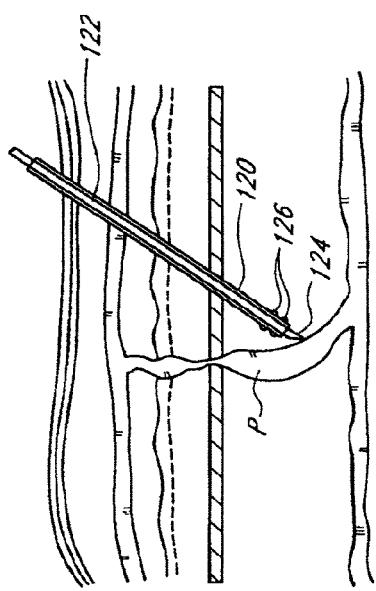
Figure 12D:
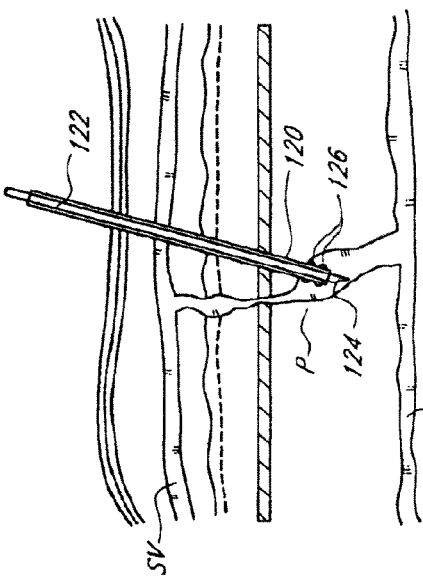

To this point, several devices and protocols for introducing rigid and non-rigid probes through an introducer sheath, cannula, or catheter have been described. As shown in FIGS. 12A-12D, however, it is also possible to introduce electrode structures on the exterior of a rigid or non-rigid probe "directly". Direct access is achieved using probe 120 having a needle or trocar 122 in a central lumen thereof or having a sharpened distal electrode being rigidly fixed to the probe as in FIG. 6. The needle or trocar 122 has a sharpened distal tip 124 which allows direct penetration through the tissue until the sharpened tip 124 reaches the perforator vein P or other HAS. The sharpened tip 124 is then used to penetrate the HAS, as shown in FIG. 12B. The needle or trocar 122 may then be retracted to within the probe 120, and radiofrequency energy delivered through the electrodes 126, as shown in FIG. 12C. The energy causes constriction CON of the perforator vein P or other HAS as shown in FIG. 12D. After the treatment is complete, the probe 120 may be withdrawn. The protocol illustrated in FIGS. 12A-12D could also be performed using a single polarity and/or electrode device. Additionally, the protocol illustrated could also be used in performing an extravascular procedure.

Figure 13C:
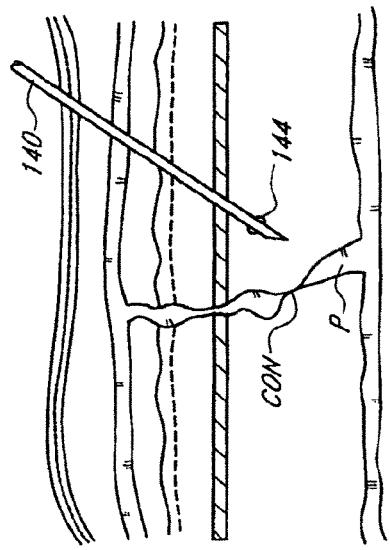
FIGS. 13A-13C illustrate the use of a rigid probe having a single electrode for penetrating and pinning a HAS in order to constrict the HAS in accordance with principles of the disclosure.
Figure 13A:
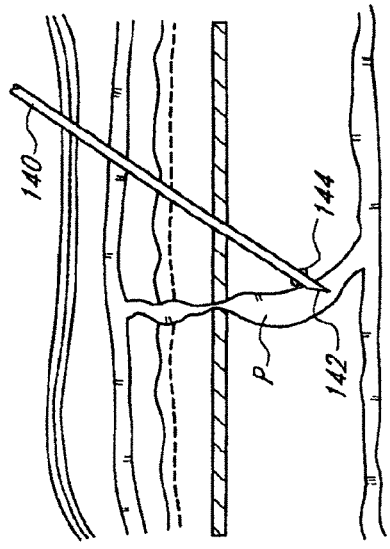
Figure 13B:
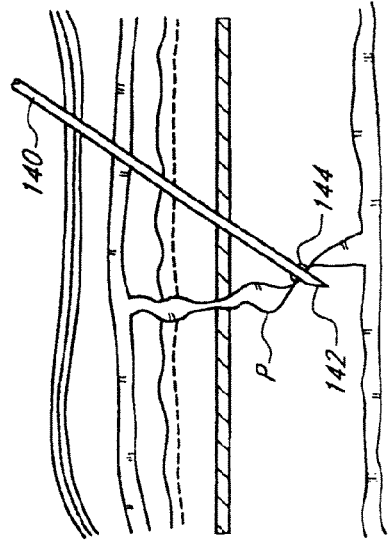

Referring now to FIGS. 13A-13C, a rigid probe 140 having a sharpened distal tip 142 and a single electrode 144 may be introduced to directly access the perforator vein P or other HAS, as shown in FIG. 13A, and to penetrate and pin the vein, as shown in FIG. 13B. Sufficient manual force is maintained on the probe 140 to collapse the perforator vein P or other HAS while energy is being delivered, as shown in FIG. 13B. The result is a constriction CON in perforator vein P or other HAS when the procedure is terminated, as shown in FIG. 13C. While the use is described in connection with the rigid single polarity and/or electrode probe 140, the method will generally apply to the other embodiments described herein.

Figure 14C:
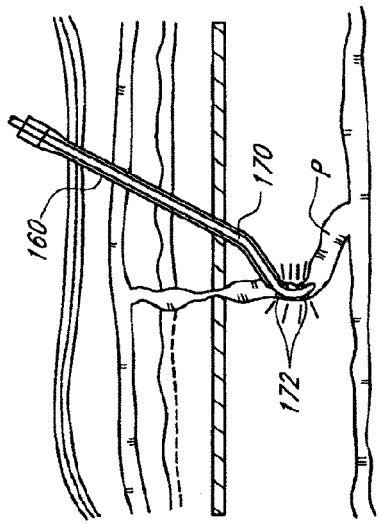
FIGS. 14A-14D illustrate the use of a flexible probe introduced through a percutaneous sheath performing an endovascular treatment of a HAS in order to constrict the HAS in accordance with principles of the disclosure.
Figure 14D:
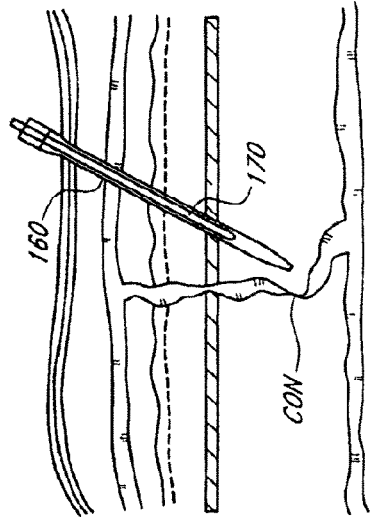
Figure 14A:
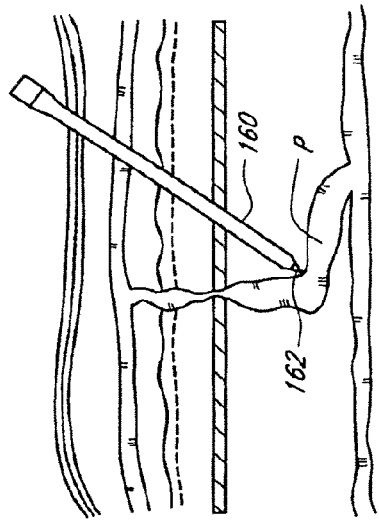
Figure 14B:
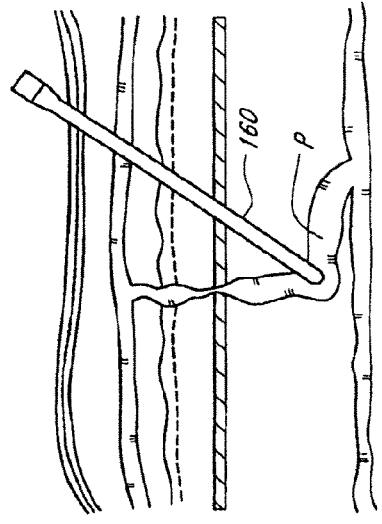

Referring now to FIGS. 14A-14D, use of a flexible instrument introduced through an introducer sheath, cannula, or catheter will be described. A conventional needle and cannula assembly 160 having a removable needle 162 may be introduced to a perforator vein P or other HAS under ultrasound guidance. The cannula 160 may be introduced into the perforator vein P or other HAS using the needle 162, and the needle withdrawn, as shown in FIG. 14B. It is contemplated that the needle may be hollow in some embodiments. A flexible probe 170 having a pair of electrodes 172 at its distal end may then be introduced through the cannula 160. The probe 170, with flexible and atraumatic tip, will align itself with the interior of the perforator vein P or other HAS lumen, as shown in FIG. 14C. The length of the flexible probe allows for distal advancement into the lumen after insertion. Energy is then delivered through the electrodes 172 to constrict CON the vein or other HAS as shown in FIG. 14D. The probe 170 is then withdrawn into the cannula 160, and the assembly withdrawn.

Figure 15A:
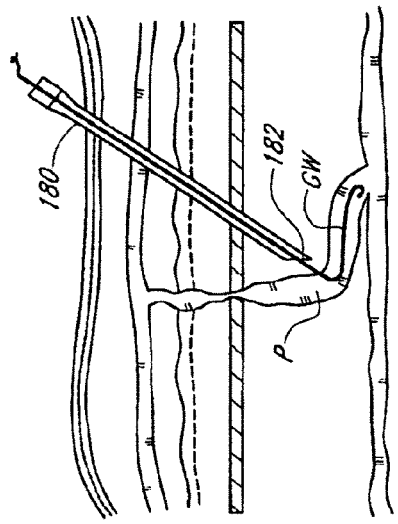
FIGS. 15A-15F illustrate the use of a small gage needle for placement of a guidewire and introduction of a two electrode probe with sliding external sheath over the guidewire in order to constrict the HAS in accordance with principles of the disclosure.
Figure 15C:
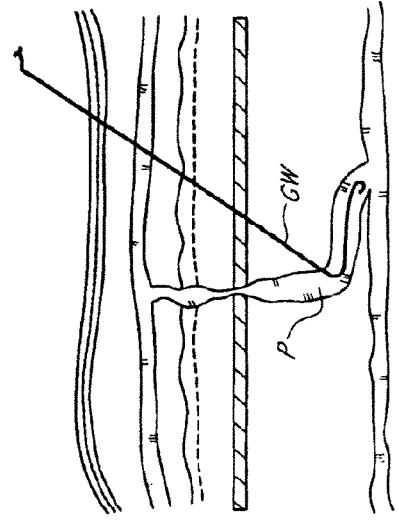
Figure 15B:
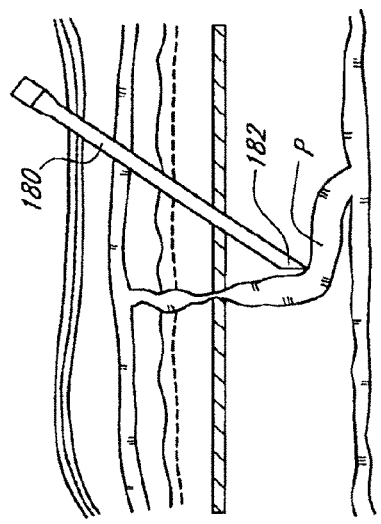
Figure 15D:
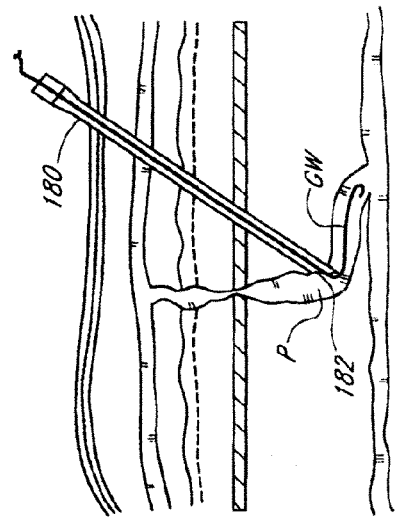
Figure 15E:
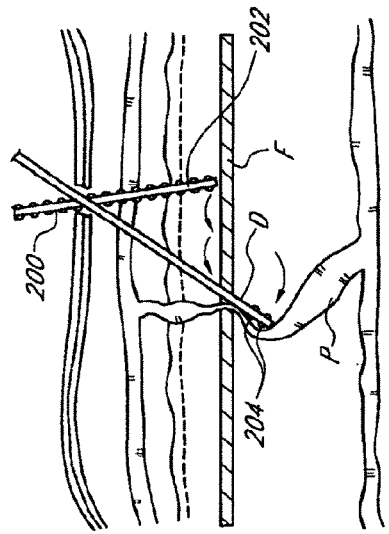
Figure 15F:
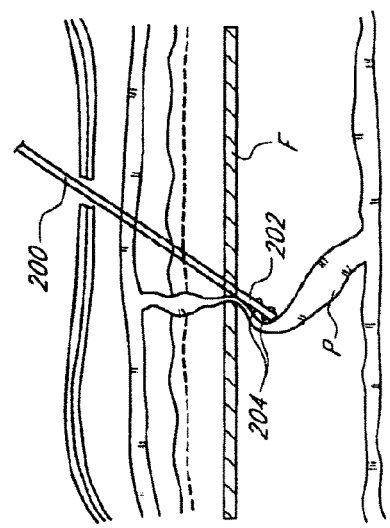

Endovascular procedures may also be performed over a guidewire GW introduced through an introducer sheath, cannula, or catheter 180 which may be introduced over a needle (not shown) in a conventional manner. Optionally, the guidewire GW may be introduced directly through the needle. While the use is described in connection with a bipolar electrode probe, the method will generally apply to the other embodiments described herein. Referring now to FIGS. 15A-15F, the needle 180 is introduced so that its distal end 182 enters the lumen of the perforator vein P or other HAS, as shown in FIG. 15B. The guidewire GW is then introduced through the needle 180, and the needle withdrawn, as shown in FIG. 15C, leaving the guidewire GW in place through the tissue, as shown in FIG. 15D. A combination flexible probe with rigid sliding external sheath 186 is then introduced over the guidewire GW, as shown in FIG. 15E. The sliding external sheath may be partially or fully retracted to expose a distal length of the flexible probe to allow for further advancement into the HAS or to simply remove the rigid structure during treatment (not shown). Radiofrequency energy is delivered through the electrodes 188 to constrict the perforator vein P or other HAS, as shown in FIG. 15F. The sheath and probe 186 may then be withdrawn. As illustrated, the probe 186 has a flexible shaft, but it could also be rigid.

Figure 16A:
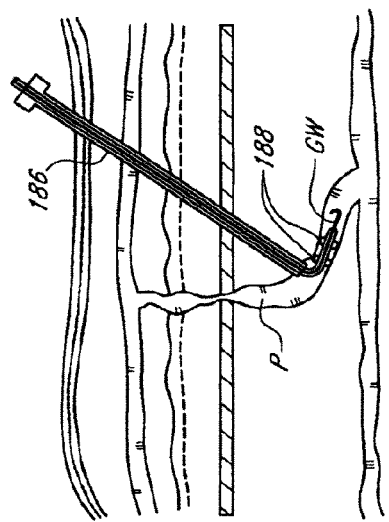
FIGS. 16A and 16B illustrate a particular method for introducing a two electrode probe to the fascial layer and moving the probe until the defect in the fascial layer is detected and the probe is introduced through the defect to a location adjacent to a HAS in order to constrict the HAS in accordance with principles of the disclosure.
Figure 16B:
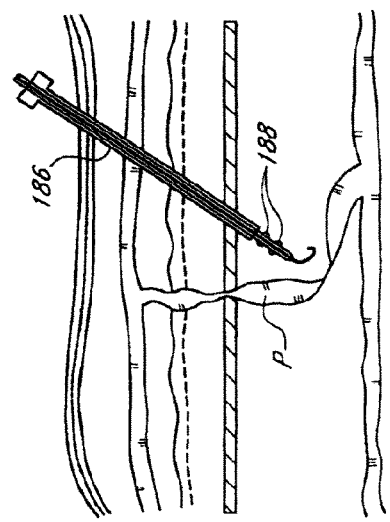

To this point, the access protocols have all involved penetrating the tissue using a needle, cannula, trocar, or other penetrating instrument. Such penetration generally requires ultrasonic or other image guidance in order to properly locate the perforator vein or other HAS and initiate treatment. As an alternative to this approach, as illustrated in FIGS. 16A and 16B, a probe 200 may be introduced through overlying tissue until its distal tip 202 encounters the fascial layer F, as shown in FIG. 16A. Initially, as shown in broken line, the probe 200 will almost certainly encounter a region of the fascia remote from the defect D through which the perforator vein P or other HAS passes. By properly moving or "dottering" the tip 202 of the probe over the fascial layer, as shown in FIG. 16A, eventually the probe will encounter the defect and pass therethrough. Once the distal end of the probe has passed through the defect, the electrodes 204 will be properly positioned adjacent the extravascular wall of the perforator vein P or other HAS, as shown in FIG. 16B. Additional manipulation, such as conical rotation of the probe 200, may allow the perforator vein P or other HAS to become wrapped around the electrode portion of the probe 200. Another form of manipulation may include using the probe 200 as a lever to press the perforator vein P or other HAS against the fascial layer from below. Radiofrequency energy can then be delivered to constrict the HAS. As with all previous protocols, the probe 200 may then be withdrawn after the treatment is complete. As illustrated, the probe 200 has a rigid shaft, but it could also be a flexible or combination flexible probe with sliding external rigid sheath. Additionally, while the use is described in connection with a bipolar electrode probe, the method will generally apply to the other embodiments described herein.

FIGS. 17-18 depict another electrode configuration 300 which can be used in any of the embodiments of the electrode probes 12, 120, 140, etc. disclosed herein, or in any suitable electrode probe, or in any of the embodiments of the system 10 disclosed herein. An electrode probe employing the electrode configuration 300 can be used in practicing any of the embodiments of the protocols disclosed herein, e.g., in practicing any of the treatment methods disclosed herein, and/or any one or more of the protocols depicted in FIGS. 8A-8D; 9A-9C; 10A-10E; 11A-11B; 12A-12D; 13A-13C; and/or 14A-14D. Except as otherwise disclosed herein, the electrode configuration 300 of FIGS. 17-18 can be generally similar to any of the electrode designs or configurations disclosed herein.

The electrode configuration 300 comprises a proximal electrode 302 and a distal electrode 304 which are separated by an electrically insulative spacer 306. An electrically insulative layer 308 extends proximally from the proximal electrode 302. A trocar or needle 350 is removably received within a lumen of the probe on which the electrodes 302, 304 are mounted. The distal electrode 304 has a distal taper 320 to ease insertion of the electrode 304 and probe through the patient's tissues. In one embodiment, the taper 320 comprises a truncated cone with a taper angle of 70 degrees referenced from a plane located distal of the electrodes and normal to the electrodes' center axis; however, in other embodiments the taper angle may be between 45 and 85 degrees. Proximal of the taper 320 is a curved electrode surface 322 of the distal electrode 304. In one embodiment, the radius of the curved electrode surface 322 is about 0.063 inches (in the sectional plane depicted in FIGS. 17-18); however, in other embodiments this radius may be between 0.040 and 0.080 inches. In one embodiment, the proximal electrode 302 also forms a curved electrode surface 330. The radius of this curved electrode surface 330 can be, in various embodiments, about 0.063 inches (in the sectional plane depicted in FIGS. 17-18), or between 0.040 and 0.080 inches.

In one embodiment, the electrode configuration 300 may take on the following dimensions: exposed axial length (i.e., the length measured along a direction parallel to the longitudinal axis of the electrode configuration 300) of the distal electrode 304=0.070 inches; maximum diameter of the distal electrode 304 and proximal electrode 302=0.077 inches; inner lumen diameter of the distal electrode 304=0.0370 inches; exposed axial length of the proximal electrode 302=0.035 inches.

Figure 19:
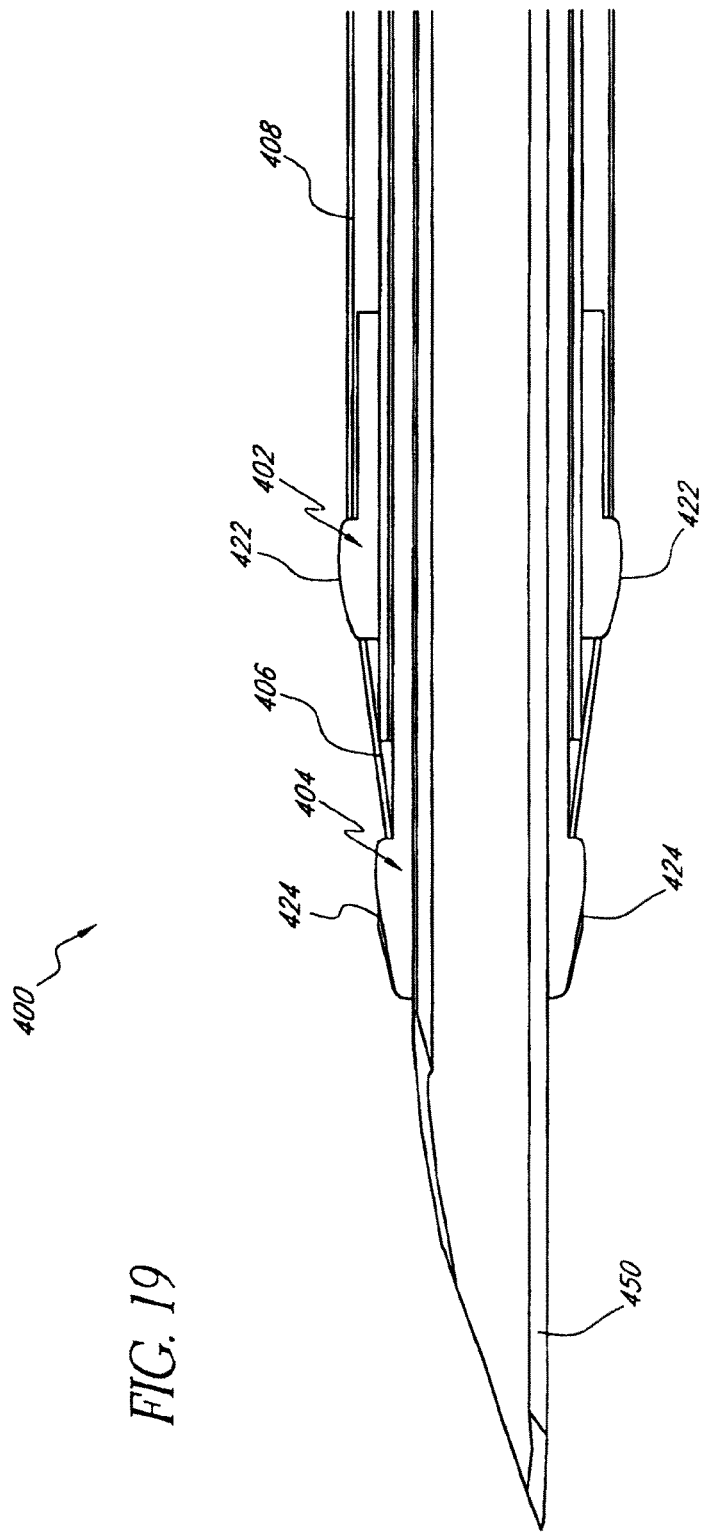
FIGS. 19 and 20 illustrate another electrode configuration suitable for use with various embodiments of the electrode probe disclosed herein.
Figure 20:
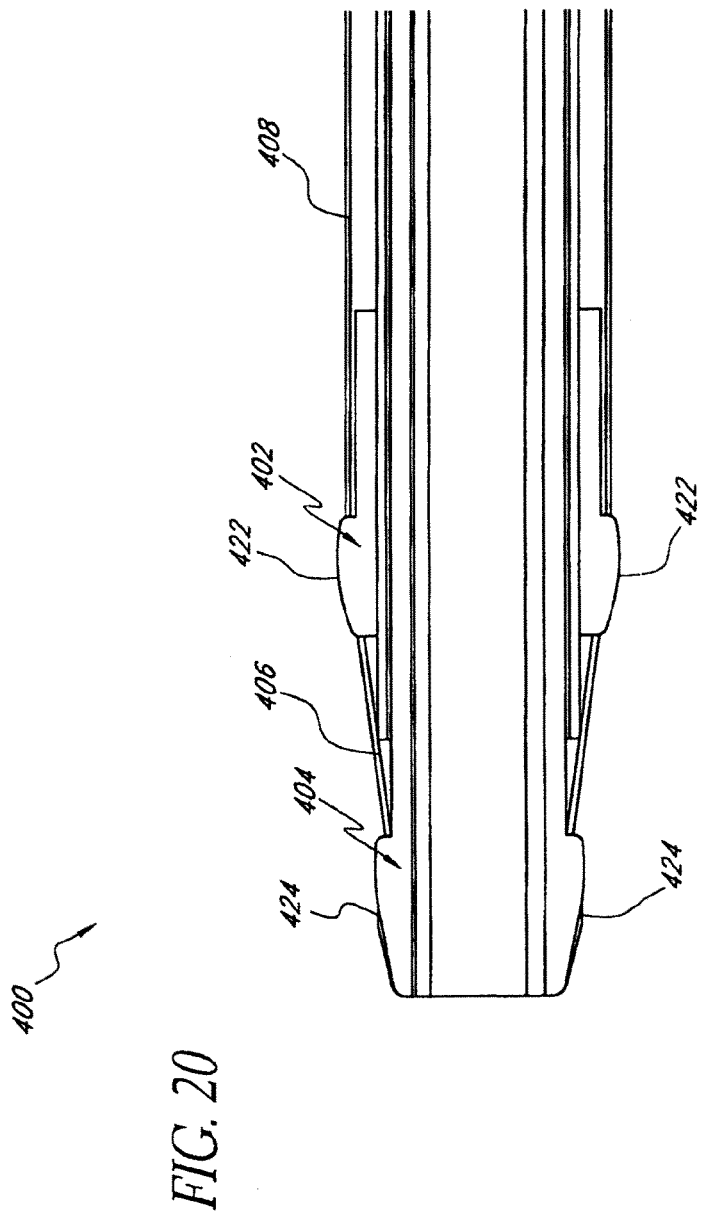

FIGS. 19-20 depict another electrode configuration 400 which can be used in any of the embodiments of the electrode probes 12, 120, 140, etc. disclosed herein, or in any suitable electrode probe, or in any of the embodiments of the system 10 disclosed herein. An electrode probe employing the electrode configuration 400 can be used in practicing any of the embodiments of the protocols disclosed herein, e.g., in practicing any one or more of the protocols depicted in FIGS. 8A-8D; 9A-9C; 10A-100E; 11A-11B; 12A-12D; 13A-13C; and/or 14A-14D. Except as otherwise disclosed herein, the electrode configuration 400 of FIGS. 19-20 can be generally similar to any of the electrode designs or configurations disclosed herein.

The electrode configuration 400 comprises a proximal electrode 402 and a distal electrode 404 which are separated by an electrically insulative spacer 406. An electrically insulative layer 408 extends proximally from the proximal electrode 402. A trocar or needle 450 is removably received within a lumen of the probe on which the electrodes 402, 404 are mounted. Each of the electrodes 402, 404 has a corresponding curved, tapered outer surface 422, 424 to ease insertion of the electrodes 402, 404 and probe through the patient's tissues. Each of the outer surfaces of the electrodes 402, 404 is tapered in that the diameter of each outer surface 422, 424 is greater at the proximal end than at the distal end thereof.

In one embodiment, the outer surface 422 of the proximal electrode 402 tapers from a diameter of 0.075 inches at its proximal end to a diameter of 0.068 inches at its distal end, over an exposed axial length of 0.035 inches, while the outer surface 422 has a maximum diameter of 0.077 inches between the distal and proximal ends. These dimensions may vary as needed in other embodiments. In one embodiment, the outer surface 424 of the distal electrode 404 tapers from a diameter of 0.0552 inches at its proximal end to a diameter of 0.045 inches at its distal end, over an exposed axial length of 0.047 inches, while the outer surface 424 has a maximum diameter of 0.0565 inches between the distal and proximal ends. These dimensions may vary as needed in other embodiments.

In one embodiment, the radius of the outer surface 422 of the proximal electrode 402 is 0.063 inches in the sectional plane depicted in FIGS. 19-20, and the radius of the outer surface 424 of the distal electrode 404 is 0.113 inches in the sectional plane depicted in FIGS. 19-20.

In one embodiment, the electrically insulative spacer 406 is tapered to provide a smooth graduation between the proximal electrode 402 and the distal electrode 404.

In one embodiment, the inner lumen diameter of the distal electrode 404 is 0.0370 inches.

In one embodiment, the exposed surface area of the outer surface 422 of the proximal electrode 402 is approximately equal to the exposed surface area of the outer surface 424 of the distal electrode 404.

Figure 21:
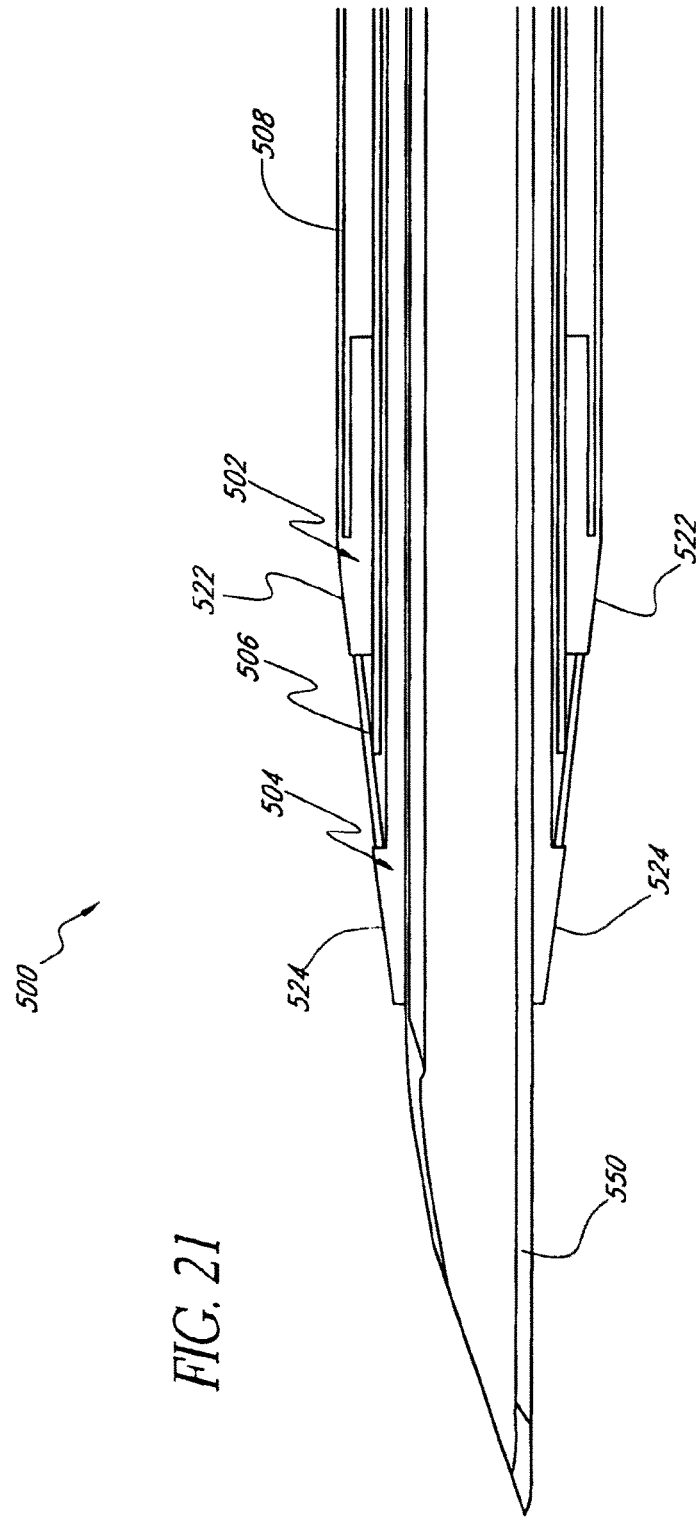
FIGS. 21 and 22 illustrate another electrode configuration suitable for use with various embodiments of the electrode probe disclosed herein.
Figure 22:
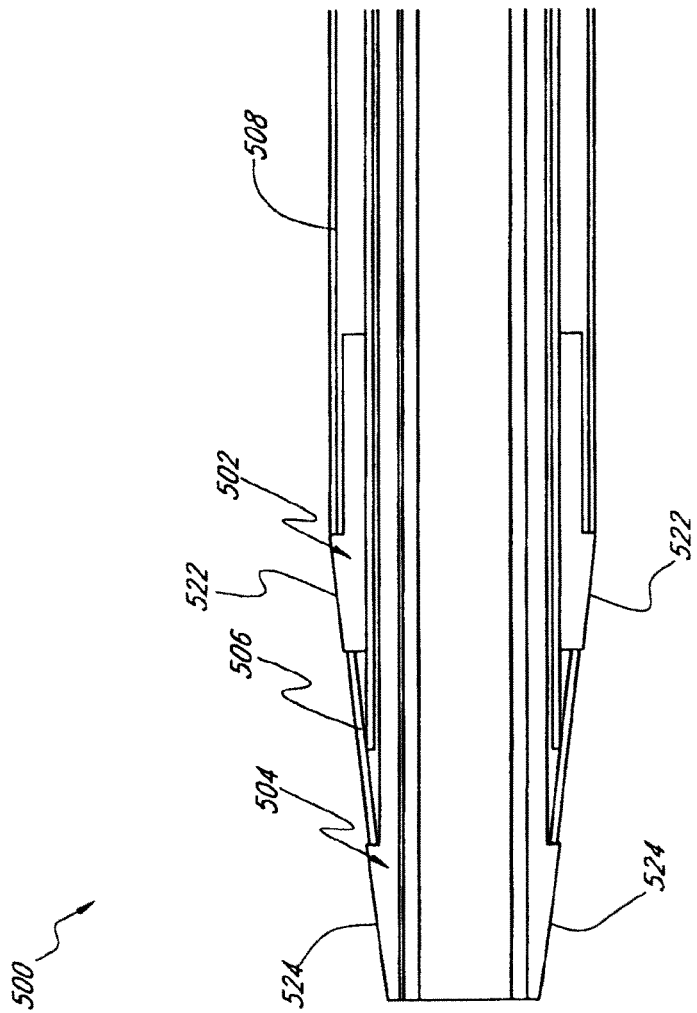

FIGS. 21-22 depict another electrode configuration 500 which can be used in any of the embodiments of the electrode probes 12, 120, 140, etc. disclosed herein, or in any suitable electrode probe, or in any of the embodiments of the system 10 disclosed herein. An electrode probe employing the electrode configuration 500 can be used in practicing any of the embodiments of the protocols disclosed herein, e.g., in practicing any one or more of the protocols depicted in FIGS. 8A-8D; 9A-9C; 10A-10E; 11A-11B; 12A-12D; 13A-13C; and/or 14A-14D. Except as otherwise disclosed herein, the electrode configuration 500 of FIGS. 21-22 can be generally similar to any of the electrode designs or configurations disclosed herein.

The electrode configuration 500 comprises a proximal electrode 502 and a distal electrode 504 which are separated by an electrically insulative spacer 506. An electrically insulative layer 508 extends proximally from the proximal electrode 502. A trocar or needle 550 is removably received within a lumen of the probe on which the electrodes 502, 504 are mounted.

Each of the electrodes 502, 504 has a corresponding tapered outer surface 522, 524 to ease insertion of the electrodes 502, 504 and probe through the patient's tissues. Each of the outer surfaces of electrodes 502, 504 is tapered in that the diameter of each outer surface 522, 524 is greater at the proximal end than at the distal end thereof.

The outer surfaces 522, 524 are "flat tapered" in that each defines a truncated cone or frustum with a taper angle of 84 degrees referenced from a plane located distal of the electrodes and normal to the electrodes' center axis. In other embodiments, this taper angle can vary between 70 and 88 degrees.

In one embodiment, the outer surface 522 of the proximal electrode 502 tapers from a diameter of 0.075 inches at its proximal end to a diameter of 0.068 inches at its distal end, over an exposed axial length of 0.035 inches. These dimensions may vary as needed in other embodiments. In one embodiment, the outer surface 524 of the distal electrode 504 tapers from a diameter of 0.0552 inches at its proximal end to a diameter of 0.045 inches at its distal end, over an exposed axial length of 0.047 inches. These dimensions may vary as needed in other embodiments.

In one embodiment, the electrically insulative spacer 506 is tapered to provide a smooth graduation between the proximal electrode 502 and the distal electrode 504.

In one embodiment, the inner lumen diameter of the distal electrode 504 is 0.0370 inches.

In one embodiment, the exposed surface area of the outer surface 522 of the proximal electrode 502 is approximately equal to the exposed surface area of the outer surface 524 of the distal electrode 504.

Figure 23:
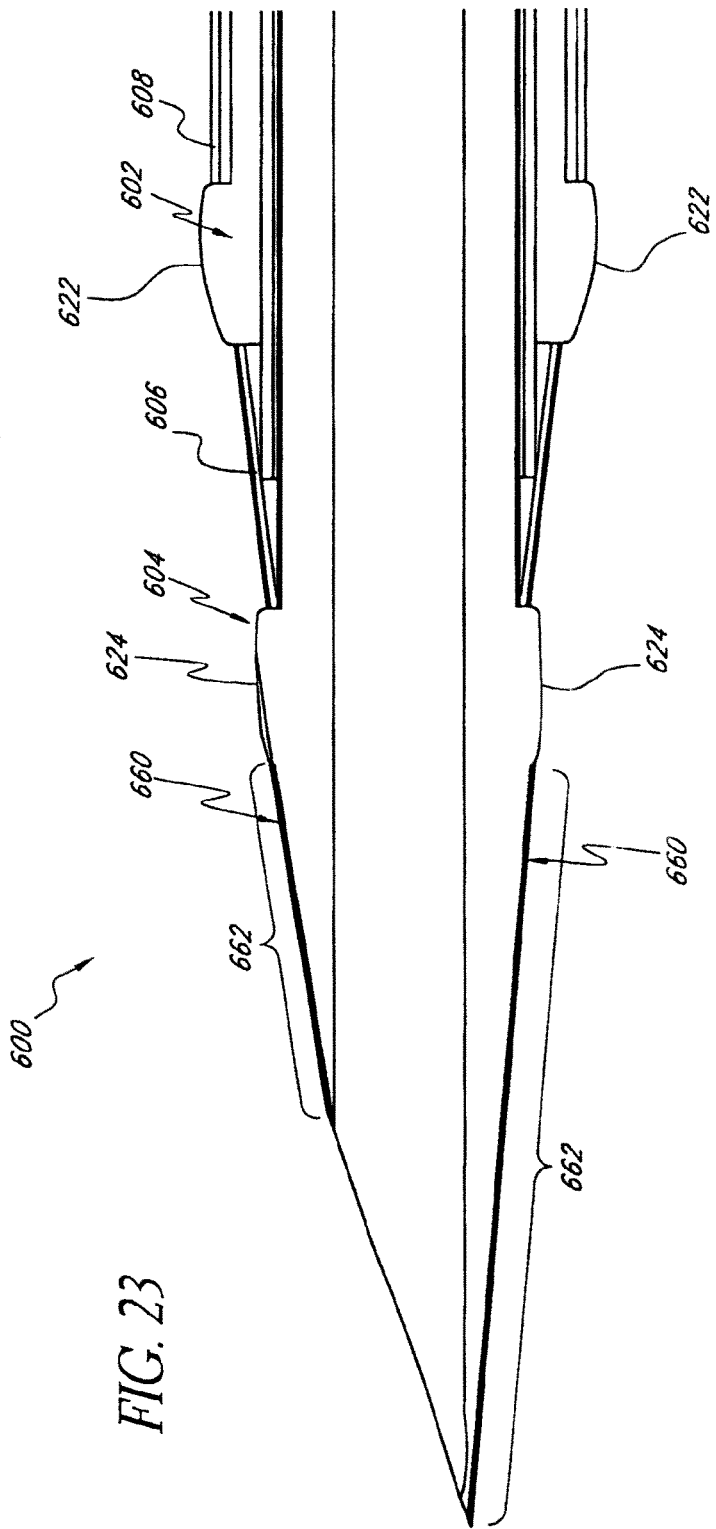
FIG. 23 illustrates another electrode configuration suitable for use with various embodiments of the electrode probe disclosed herein.

FIG. 23 depicts another electrode configuration 600 which can be used in any of the embodiments of the electrode probes 12, 120, 140, etc. disclosed herein, or in any suitable electrode probe, or in any of the embodiments of the system 10 disclosed herein. An electrode probe employing the electrode configuration 600 can be used in practicing any of the embodiments of the protocols disclosed herein, e.g., in practicing any one or more of the protocols depicted in FIGS. 8A-8D; 9A-9C; 10A-100E; 11A-1B; 12A-12D; 13A-13C; and/or 14A-14D. Except as otherwise disclosed herein, the electrode configuration 600 of FIG. 23 can be generally similar to any of the electrode designs or configurations disclosed herein.

The electrode configuration 600 comprises a proximal electrode 602 and a distal electrode 604 which are separated by an electrically insulative spacer 606. An electrically insulative layer 608 extends proximally from the proximal electrode 602.

The distal electrode 604 is integrally formed with a sharp entry tip 660 which extends distally from the distal end of the distal electrode 604. The entry tip 660 is appropriately tapered and sharpened to facilitate passage of the electrodes 602, 604 and probe through the tissues of the patient. The outer surface 662 of the entry tip may be electrically insulated to isolate the function of the distal electrode 604 to the desired region.

Each of the electrodes 602, 604 preferably has a corresponding exposed, curved, tapered outer surface 622, 624 to further ease insertion of the electrodes 602, 604 and probe through the patient's tissues. Each of the outer surfaces of electrodes 602, 604 is tapered in that the diameter of each outer surface 622, 624 is greater at the proximal end than at the distal end thereof.

In the depicted embodiment, the electrodes 602, 604 and outer surfaces 622, 624 thereof have shapes and dimensions which are similar to those of the electrodes 402, 404 (and the outer surfaces 422, 424 thereof) of the configuration 400 shown in FIGS. 19-20. However, in other embodiments, the electrodes 602, 604 and outer surfaces 622, 624 thereof can take on other suitable shapes and dimensions. For example, the shapes and dimensions of the electrodes 502, 504 (and the outer surfaces 522, 524 thereof) of the configuration 500 shown in FIGS. 21-22 may be employed as an alternative.

In one embodiment, the electrically insulative spacer 606 is tapered to provide a smooth graduation between the proximal electrode 602 and the distal electrode 604.

In one embodiment, the inner lumen diameter of the distal electrode 604 is 0.0370 inches.

In one embodiment, the exposed surface area of the outer surface 622 of the proximal electrode 602 is approximately equal to the exposed surface area of the outer surface 624 of the distal electrode 604.

FIG. 24 depicts a resistive-element tip 700 which can be used in any of the embodiments of the electrode probes 12, 120, 140, etc. disclosed herein, in place of (or in addition to) the electrodes. The tip 700 comprises a resistive-element heater 702 mounted on a distal section 704 of the probe. The distal section 704 with heating element 702 may be tapered or cylindrical or tapered distally and cylindrical proximally. In use, the heater 702 is heated by passing electrical current therethrough and the hot heater 702 can be used to heat the inner lumen of a vein to close the vein. Thus, a probe employing the resistive-element tip 700 can be used in practicing any of the embodiments of the protocols disclosed herein, e.g., in practicing any one or more of the protocols depicted in FIGS. 8A-8D; 9A-9C; 10A-10E; 11A-11B; 12A-12D; 13A-13C; and/or 14A-14D, with the exception that thermal energy is applied via the resistive-element tip 700 instead of RF power applied via electrodes.

The resistive-element heater 702 can comprise a simple coil of resistive-heating material or wire, or a series of axially adjacent, separately operable coils. Such separate coils can be operated sequentially or in overlapping sequential groups, or in a fixed subset to vary the treatment length and/or minimize the power requirements of the heater. Each coil can have a separate temperature sensor to facilitate such separate operation and control. In other embodiments, the structure and/or operation of the heater 702 can be similar to any of the various embodiments of resistive elements or heaters, and/or modes of operation thereof, disclosed in U.S. Provisional Application No. 60/613,415, filed Sep. 27, 2004, titled RESISTIVE ELEMENT SYSTEM. The entire disclosure of the above-mentioned provisional application is hereby incorporated by reference herein and made a part of this specification.

A trocar or needle 750 is removably received (or, alternatively, fixedly received) within a lumen of the probe on which the heater 702 is mounted.

While the above is a complete description of the preferred embodiments of the invention, various alternatives, modifications, and equivalents may be used. Therefore, the above description should not be taken as limiting the scope of the invention which is defined by the appended claims.

What is claimed is:
1. A method of treating a perforator vein comprising:
achieving direct percutaneous access into tissue with a rigid stylet having a resistive heating coil forming a portion of an exterior surface of the stylet, and a sharp tip, the resistive heating coil being covered by an electrically insulative sleeve;

advancing the stylet below a fascial layer and to a portion of the perforator vein below the fascial layer, the fascial layer comprising deep fascia through which the perforator vein passes to connect a superficial vein with a deep vein; and occluding the perforator vein by applying energy from the resistive heating coil to the portion of the perforator vein below the fascial layer.

2. The method of claim 1, wherein achieving direct percutaneous access is done without the use of an introducer sheath.

3. The method of claim 1, wherein occluding further comprises applying energy to an exterior surface of the perforator vein.

4. The method of claim 1, wherein occluding further comprises applying energy to an interior vessel wall of the perforator vein.

5. The method of claim 1, wherein the sharp tip is fixedly received within the stylet.

6. The method of claim 1, wherein the resistive heating coil is at a distal section of the stylet.

7. The method of claim 1, wherein the resistive heating coil is tapered.

8. The method of claim 1, wherein the advancing and occluding are performed under ultrasound guidance.

9. The method of claim 1, further comprising conically rotating the stylet to wrap the perforator vein around the stylet.

10. A method comprising:
directly accessing a target site with a rigid probe through the skin, the target site being within or near a perforator vein, the rigid probe comprising:
a tapered resistive heating coil on an outside surface of and near a distal end of the probe;
a nonconductive sleeve on an outside surface of the resistive heating coil; and
a sharp tip at the distal end of the probe and configured to penetrate tissue;

retracting the sharp tip within the probe;

after retracting the sharp tip within the probe, applying heat energy from the resistive heating coil to the perforator vein with the probe; and constricting a region of the perforator vein.

11. The method of claim 10, wherein applying heat energy comprises applying heat energy to an exterior surface of the perforator vein.

12. The method of claim 10, wherein applying heat energy comprises applying heat energy to an interior vessel wall of the perforator vein.

13. The method of claim 10, further comprising constricting additional regions of the perforator vein.

14. A method comprising:
achieving direct access with a rigid probe through the skin to a target site within or near a perforator vein, the rigid probe comprising:
a sharp tip at a distal end of the probe and configured to penetrate tissue; and
a resistive heating coil proximal of the sharp tip, the resistive heating coil being covered by an electrically insulative sleeve;

retracting the sharp tip within the probe;

applying energy to the perforator vein with the resistive heating coil; and constricting a region of the perforator vein;

further comprising fully penetrating the perforator vein so that the sharp tip passes all the way through the perforator vein to a far side of the perforator vein, applying energy as the probe is drawn back from the far side of the perforator vein and through the perforator vein, and constricting the region of the perforator vein as the probe is withdrawn from the perforator vein.

15. The method of claim 14, wherein the method further comprises positioning the resistive heating coil adjacent an exterior of the vein.

* * * * *